(12) United States Patent
Yu

(10) Patent No.: US 7,927,612 B2
(45) Date of Patent: *Apr. 19, 2011

(54) COMBINATIONS AND METHODS FOR TREATING NEOPLASMS

(75) Inventor: Baofa Yu, San Diego, CA (US)

(73) Assignee: Baofa Yu, San Diego, CA (US)

( * ) Notice: Subject to any disclaimer, the term of this patent is extended or adjusted under 35 U.S.C. 154(b) by 1683 days.

This patent is subject to a terminal disclaimer.

(21) Appl. No.: 10/973,798

(22) Filed: Oct. 25, 2004

(65) Prior Publication Data

US 2005/0118187 A1 Jun. 2, 2005

Related U.S. Application Data

(63) Continuation-in-part of application No. 09/765,060, filed on Jan. 17, 2001, now Pat. No. 6,811,788.

(60) Provisional application No. 60/177,024, filed on Jan. 19, 2000.

(51) Int. Cl.
*A61K 39/39* (2006.01)
*A61K 39/385* (2006.01)
*A61K 45/00* (2006.01)
*A61K 1/02* (2006.01)

(52) U.S. Cl. .................... 424/278.1; 424/1.11; 424/1.57; 424/573

(58) Field of Classification Search .................... None
See application file for complete search history.

(56) References Cited

U.S. PATENT DOCUMENTS

| | | | | |
|---|---|---|---|---|
| 4,160,817 A | * | 7/1979 | Bucovaz et al. | 436/504 |
| 4,447,526 A | | 5/1984 | Rupchock et al. | 435/7 |
| 4,724,230 A | | 2/1988 | Cone, Jr. | 514/558 |
| 4,832,849 A | * | 5/1989 | Cardin | 210/635 |
| 4,971,991 A | | 11/1990 | Umemura et al. | |
| 5,005,588 A | | 4/1991 | Rubin | 128/804 |
| 5,156,841 A | | 10/1992 | Rapp | 424/277.1 |
| 5,215,899 A | | 6/1993 | Dattagupta | 435/6 |
| 5,290,551 A | | 3/1994 | Berd | 424/88 |
| 5,340,803 A | * | 8/1994 | Rubin | 514/25 |
| 5,651,986 A | | 7/1997 | Brem et al. | 424/484 |
| 5,705,151 A | | 1/1998 | Dow et al. | 424/93.21 |
| 5,846,565 A | | 12/1998 | Brem et al. | 424/486 |
| 6,248,585 B1 | * | 6/2001 | Berd | 435/325 |
| 7,041,302 B2 | * | 5/2006 | Roussel | 424/278.1 |

FOREIGN PATENT DOCUMENTS

| | | |
|---|---|---|
| EP | 240191 | 10/1987 |
| EP | 378888 | 7/1990 |
| FR | 2505182 | 11/1982 |
| JP | 11-171788 | 6/1999 |
| WO | WO96/39226 | * 12/1996 |
| WO | WO 97/11666 | 4/1997 |
| WO | WO 98/03195 | 1/1998 |
| WO | WO 98/40105 | 9/1998 |
| WO | WO 99/46385 | 9/1999 |
| WO | WO 00/06143 | 2/2000 |

OTHER PUBLICATIONS

Abstract of Schneider et al, Gene Ther, 1999, vol. 6, suppl. 1, S5).*
Drug Facts and Comparisons, T. Burnham, Ed., 2000, p. 1807.*
Martin et al, Archives of Biochemistry and Biophysics, 1987, vol. 255, pp. 329-336.*
Clark (Protein Engineering of Antibody Molecules for Prophylactic and Therapeutic Applications in Man, 1993, pp. 4-5).*
Abstract of Uehara, Can to kagaku ryoho, 1997, vol. 24, pp. 136-144.*
Dasgupta et al, Experimental Cell Research, 1997, vol. 237, pp. 29-37.*
Gong et al (Journal of biological Chemistry, 2000, vol. 275, pp. 3355-3359).*
Barbie et al (Trends in Cell biology, 2005, vol. 15, pp. 378-385).*
Jones et al., Advanced Drug Delivery Reviews 1998, p. 160,section 3).*
Verma et al (Nature, 1997, vol. 389, pp. 239-242).*
Orkin ( "Report and Recommendation of the Panel to Assess the NIH Investment in Research on Gene Therapy", NIH, 1995).*
Tolcher et al (Clinical Cancer Research, 2002, vol. 8, pp. 2530-2535).*
Cripps et al (Clinical Cancer Research. 2002, 8, pp. 2188-2192).*
Marshall et al (Clinical Colorectal Cancer, 2004, vol. 4, pp. 268-274).*
Oza et al (Gynecological Oncology, 2003, vol. 89, pp. 129-133).*
Paul, Fundamental Immunology, (text), 1993, pp. 1157-1170).*
Abstract, Ferguson et al, Int Review Immunol, 2002, vol. 21, pp. 153-172, lines 9-12).*
Cotton and Wilkinson (Advanced Inorganic Chemistry (text), 1972, p. 408).*
E. Vadas, 'Stability of Pharmaceutical Products' in: Remmington: The Science and Practise of Pharmacy, 19th Ed., 1995, pp. 639-647.*
1999 Edition of the Sigma Catalog, p. 2399.*
Abstract of Coxon et al (Ann Clin Biochem, Jan. 1988, 25(pt 1), pp. 49-52).*
Abstract of Mansouri (BBRC, 1979, vol. 89(2), pp. 441-447).*
NLM Mesh Term information for Cytarabine, downloaded May 26, 2008.*
Remington: The Science and Practice of Pharmacy, 1995, pp. 1529-1530.*
Orkin et al., "Report and Recommendation of the Panel to Assess the NIH Investment in Research on Gene Therapy," NIH, 1995.
Reiger et al., eds., Glossary of Genetics, Classical and Molecular, 5$^{th}$ ed., (1991) p. 422.

(Continued)

*Primary Examiner* — Karen A Canella
(74) *Attorney, Agent, or Firm* — Knobbe Martens Olson & Bear LLP

(57) ABSTRACT

Methods for treating neoplasms, tumors and cancers, using one or more haptens and coagulation agents or treatments, alone or in combination with other anti-neoplastic agents or treatments, are provided. Also provided are combinations, and kits containing the combinations for effecting the therapy.

26 Claims, 3 Drawing Sheets

OTHER PUBLICATIONS

Ferguson et al., Int. Review Immunol. (2002) 21:153-172.
Paul, Fundamental Immunology (1993) pp. 705-706, 930, 990-992.
Schneider et al., Gene Ther. (1999) 6(1):S5.
Verma et al., Nature (1997) 389:239-242.
Eck et al., Gene-Based Therapy, in The Pharmacological Basis of Therapeutics, Goodman and Gilman, (eds.), (1996) pp. 77-10.
Lisowski et al., J. Immunological Methods (1972) 1:341-352.
Todryk et al., J. Immunology (1999) 163:1398-1408.
Lin et al., J. Gastroenterology and Hepatology (1997) 12:S319-S328.
Molloy et al., J. Experimental Medicine (1994) 180:1499-1509.
Brien et al., Lasers in Surgery and Medicine (1992) 12:313-317.
Martin et al., Archives in Biochemistry and Biophysics (1987) 255:329-336.
Dima et al., Laser Therapy (1990) 2:153-160.
Krosl et al., Cancer Research (1996) 56:3281-3286.
Skobelkin et al., Laser Therapy (1991) 3:169-175.
Pan et al., Cancer Research (1989) 49:5048-5053.
Adams. Poult. Sci. 49(1):229-33 (1970).
Auerbach. Pharmacol. Ther. 63(3):265-311 (1994).
August. Clin. Dermatol. 13(6):589-92 (1995).
Aw. "Molecular and Cellular Responses to Oxidative Stress and Changes in Oxidation-Reduction Imbalance in the Intestine" (Abstract) at <http://www.ajcn.org> (visited on Jun. 6, 2002).
Awwad et al. Cancer Immunol. Immunother. 38:23-30 (1994).
Berd, et al. Cancer Research 46:2572-2577 (1986).
Berd et al. Cancer Research 51:2731-2734 (1991).
Berd et al. Journal of Clinical Oncology 15(6):2359-2370 (1997).
Berd et al. Seminars in Oncology 25(6):646-653 (1998).
Berd. Seminars in Oncology 25(6):605-610 (1998).
Bier et al. "Intratumor Immunotherapy with BCG Cell Wall Preparations: Development of a New Therapy Approach for Head-Neck Tumors" (abstract) at <http://www.ncbi.nim.nih.gov> (visited on Nov. 24, 1999).
Bingya et al. Chin. J. Oncol. 20(1):34-36 (1998).
Biochemistry 11(9):1726 (1972).
Bromberg et al. The Cancer Journal from Scientific American pp. 132-138 (1999).
Brunschwig et al. J. Immunother. 22(5):390-400 (1999).
Chakraborty et al. Cancer Immunol. Immunother. 47:58-64 (1998).
Calsini et al. "Immunotherapy of Bladder Cancer with Intralesional Injection with BCG" (Abstract) at <http://www.ncbi.nlm.nih.gov> (visited on Nov. 24, 1999).
Chamberlain. Drugs 57)3):309-325 (1999).
Chang et al. Int. J. Radiat. Oncol. Biol. Phys. 40(1):65-70 (1998).
Chang et al. Br. J. Plast. Surg. 52(3):178-81 (1999).
Chassoux et al. "Therapeutic Effect of Intratumoral Injection of bcg and Other Substances in Rats and Mice" (Abstract) at <http://www.ncbi.nim.nih.gov> (visited on Nov. 24, 1999).
Chen et al. Journal of Biomedical Science 5:231-252 (1998).
Chen et al. The Cancer Journal from Scientific American pp. 16-17 (1999).
Claman. Journal of Immunology I16(3):704-9 (1976).
Dieli et al. Int. Immunol. 9(1):1-8 (1997).
Duda et al. Annals of Surgical Oncology 2(6):542-9 (Abstract) (1995).
Fisher at al. "Comparative Effects of *Corynebacterium parvum*, *Brucella abortus* Extract, Bacillus Calmette-Guerin, Glucan, Levamisole, and Tilorone With or Without Cyclophosphamide on Tumor Growth, Macrophage Production, and Macrophage Cytotoxicity in a Murine Mammary Tumor Model" (Abstract) at <http://www.ncbi.nlm.nih.gov> (visited on Nov. 24, 1999).
Fujiwara et al. Journal of Immunology 132(3):1571-1577 (1984).
Gavrilenko et al. Vopr. Onkol. 29(4):67-70 (1983).
Gilboa. Cancer Immunol. Immunother. 48:382-385 (1999).
Goldberg et al. Radiology 209(2):371-9 (1998).
Goldberg et al. Radiology 209(3):761-7 (1998).
Goldberg et al. Radiology 213(2):438-44 (1998).
Haas et al. "An Effective Strategy Human Tumor Vaccine Modification by Coupling Bispecific Costimulatory Molecules" (Abstract) at <http://www.cdlib.org> (visited on Nov. 28, 1999).
Haba et al. Int. J. Cancer 18(1):93-104 (1976).
Hageboutros et al. Investigational New Drugs 15:139-145 (1997).
Hawkins. Current Opinion in Oncology 7:90-93 (1995).
Helting et al. Acta Pathol. Microbiol. Immunol. Scand. 92(1):59-63 (1984).
Henderson. "Regression of Lung Metastases After Immunotherapy with Autologous, DNP-Modified Melanoma Vaccine" (Abstract) at <http://www.cdlib.org> (visited on Sep. 7, 1999).
Henderson et al. "Advances in Conventional Treatment of Breast Cancer: The Addition of BCG and Autotumour Vaccine Immunotherapy" (Abstract) at <http://www.cdlib.org> (visited on Sep. 7, 1999).
Henderson. "Cancer Immunotherapy Autologous Melanoma Cell Vaccine Generates Immunity" (Abstract) at <http://www.cdlib.org> (visited on Sep. 7, 1999).
Hess Eur. J. Immunol. 6(3):188-93 (1976).
Holmes et al. "Intralesional BCG Immunotherapy of Pulmonary Tumors" (Abstract) at <http://ncbi.nim.nih.gov> (visited on Nov. 24, 1999).
Im et al. J. Biol. Chem. 260(8):4591-7 (1985).
Inouye et al. J. Clin. Microbiol. 20(3):525-9 (1984).
Jiao et al. Br. J. Surg. 86(9):1224 (1999).
Jinglin et al. Chin. J. Oncol. 19(5):333-335 (1997).
Ziegler, J. J. Natl. Cancer Instit. 88:786-788 (1996).
Jocham. Recent Results Cancer Res. 126:135-42 (1993).
Kasuga et al. "Experimental Study on Local Immunochemotherapy" (Abstract) at <http://www.ncbi.nlm.nih.gov> (visited on Nov. 24, 1999).
Kasuga et al. "Intratumor Chemoimmunotherapy with Mitomycin C and BCG in C3H/He Mice Transplanted with MH134" (Abstract) at <http://www.ncbi.nlm.nih.gov> (visited on Nov. 24, 1999).
Katz et al. J. Immunol. 107(5):1319-28 (1971).
Kelkar et.al. "Antitumor Activity of Lactic Acid Bacteria on a Solid Fibrosarcoma, Sarcoma-180 and Ehrlich Ascites Carcinoma" (Abstract) at <http://www.ncbi.nlm.nih.gov> (visited on Nov. 24, 1999).
Klekamp et al. Arch. Biochem. Biophys. 246(2):783-800 (1986).
Krup et al. Journal of Immunotherapy 22(6):525-38 (1999).
Leong et al. Journal of Immunotherapy 22(2):166-74 (1999).
Leung et al. Immunopharmacology 35(3):255-63 (1997).
Lillehoj et al. Avian Dis. 37(3):731-40 (1993).
Marzulli et al. Boll. Soc. Ital. Biol. Sper. 61(1):121-7 (1985).
McHugh et al. Cancer Research 59:2433-7 (1999).
Menoret et al. Seminars in Oncology 25(6):654-660 (1998).
Meulemans et al. Vet. Rec. 143(11):300-3 (1998).
Miller et al. Journal of Immunology 117(5-1):1519-1526 (1976).
Mizuno et al. Biochem. Mol. Biol. Int. 47(4):707-14 (1999).
Mizuochi et al. J. Immunol. 134(2):673-6 (1985).
Nawrocki et al. Cancer Treatment Reviews 25:29-46 (1999).
Nogrady. *Medicinal Chemistry. A Biochemical Approach*, Oxford University Press, New York, pp. 388-392 (1985).
Ohmoto et al. Am. J. Roentgenol. 173(5):1231-3 (1999).
O'Reilly. Investigational New Drugs 15:5-13 (1997).
Otter et al. Cancer Immunol. Immunother. 48:419-420 (1999).
Pan et al. Biochemistry 37(5):1357-64 (1998).
Presta et al. Cancer Research 59:2417-2424 (1999).
Robinson et al. "Prostate Carcinoma: Intratumor BCG Immunotherapy" (Abstract) at <http://www.ncbi.nim.nih.gov> (visited on Nov. 24, 1999).
Saha et al. Int. J. Rad. Appl. Instrum. 16(4):431-3 (1989).
Saitoh et al. Urology 43(3):342-8 (1994).
Sakagami et al. Biochem. Biophys. Res. Commun. 155(2):650-5 (1988).
Santini et al. Free Radic. Biol. Med. 20(7):915-24 (1996).
Sato et al. Clinical Immunology and Immunopathology 85(3):265-272 (1997).
Scott et al. "Clinical Promise of Tumour Immunology" at <http://www.cdlib.org> (visited on Sep. 9, 199).
Seifert et al. World J. Surg. 23(10):1019-26 (1999).
Seiler et al. Recent Results Cancer Res. 75:53-60 (1980).
Seki et al. Am. J. Gastroenterol. 94(2):322-7 (1999).
Serrou et al. "Unanticipated Effect of BCG in Mice Treated by Radiotherapy" (Abstract) at <http://www.ncbi.nlm.nih.gov> (visited on Nov. 25, 1999).

Shchepetkin. "Hypoxic Bioreductive Agents: The Possible Immune and Receptor-Mediated Mechanisms of Antitumor Action" (Abstract) at <http://www.ncbi.nlm.nih.gov> (visited on Nov. 25, 1999).
Shields et al. Ophthalmology 105(4):581-90 (1998).
Sinn et al. Anal. Biochem. 170(1):186-92 (1988).
Sparks et al. "Effect of Isonicotinic Acid Hydrazide on the Intratumor Injection of BCG" (Abstract) at <http://www.ncbi.nim.nih.gov> (visited on Nov. 24, 1999).
Stjarnkvist et al. J. Pharm. Sci. 80(5):436-40 (1991).
Strashinin et al. Vopr. Onkol. 17(1):78-9 (1971).
Tarin et al. Mol. Hum. Reprod. 2(12):895-901 (1996).
Toda et al. Human Gene Therapy 10(3):385-93 (1999).
Vahrmeijer et al. Cancer Chemother. Pharmacol. 44(2):111-6 (1999).
Wakeling. "The Latest Weapon in the War Against Cancer (Adoptive Immunotherapy) (Cover Story)" at <http://www.cdlib.org> (visited on Sep. 7, 1999).
Watson et al. *Molecular Biology of the Gene*, 4th Edition, 1987, The Beiacmin/Cummings Pub. co., p. 224.
Wozniak et al. Bioorg. Med. Chem. Lett. 8(19):2641-6 (1998).
Yu et al. J Current Oncology 1:97-100 (1994).
Zastrow. Padiatr. Grenzgeb. 24(3):229-36 (1985).
Zhang et al. Melanoma Research 8(6):510-5 (1998) (Abstract).
E. Rudnic, "Oral Solid Dosage Forms" in: Remington's Pharmaceutical Sciences, $18^{th}$ Ed., 1990, pp. 1633-1665.
Edstrom, et al., "Mucosal Melanoma: Immunological Findings in a Rare Case Treated With BCG Vaccine, Autologous Tumor Cells, and Cytarabine" *Arch Otolaryngol* (1979) 105(1): 48-50.
Hino, et al., "Disappearance of pulmonary metastases by OK-432 treatment in a Case of Hepatocellular Carcinoma" *Acta Med Okayama* (1993) 47(4): 289-292.
Yumita, et al., "The Increase of Generation of Superoxide Radicals and the Inhibitory Effect on Yoshida Sarcoma of Anthracycline Antitumor Agents by Ultrasound" *J. Japan Society for Cancer Therapy* (1989) 24(1): 63-68. English Summary Only.

* cited by examiner

SPINAL NEEDLE

SLOWLY INJECTION

TURNING THE TOP OF NEEDLE, AROUND IN TUMOR

PREPARATION OF INJECTION CHANNELS IN TUMOR BY THE PROBE OF INJECTOR

MULTIPLE INJECTION AT ONE TIME PERIOD INJECTION AT DIFFERENT TIME

HIGH PRESSURE INJECTION BY DILOTION INJECTOR 0-6. AMP AT ONE TIME. HIGH PRESSURE SOLUTION CAN PENETRATE INTO AN EXTRACELLULAR MATRIX BETWEEN TUMOR CELLS

COMBINATIONS AND METHODS FOR TREATING NEOPLASMS

This application is a continuation-in-part of U.S. patent application Ser. No. 09/765,060, filed Jan. 17, 2001, now allowed, which claims priority benefit of the U.S. Provisional Patent Application Ser. No. 60/177,024, filed Jan. 19, 2000, entitled "COMBINATIONS AND METHODS FOR TREATING NEOPLASMS" under 35 U.S.C. §119(e), the contents of which are incorporated by reference in their entirety.

TECHNICAL FIELD

The present invention relates to compositions and methods for treating neoplasms in mammals, particularly humans. More particularly, combinations for intratumoral administrations of agents that coagulate tumors and agents that enhance the inflammatory response are provided. Also provided are methods for treating neoplasms by administration of the combinations.

BACKGROUND ART

A number of approaches, including surgery, chemotherapy and radiation, to cancer therapy have been used. Surgery is a traditional approach in which all or part of a tumor is removed from the body. Surgery generally is only effective for treating the earlier stages of cancer. For more than 50% of cancer patients by the time they are diagnosed, they are no longer candidates for effective surgical treatment. Surgical procedures may increase tumor metastases through blood circulation during surgery. Most of cancer patients do not die from the cancer at the time of diagnosis or surgery, but rather die from the metastasis and the recurrence of the cancer.

Other therapies are also often ineffective. Radiation therapy is only effective for local cancer therapy at early and middle stages of cancer, and is not effective for the late stages of cancer with metastasis. Chemotherapy can be effective, but there are severe side effects, e.g., vomiting, low white blood cells (WBC), loss of hair, loss of weight and other toxic effects. Because of the extremely toxic side effects, many cancer patients cannot successfully finish a complete chemotherapy regimen. Some cancer patients die from the chemotherapy due to poor tolerance to the chemotherapy. The extreme side effects of anticancer drugs are caused by the poor target specificity of such drugs. The drugs circulate through most normal organs of patients as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

Immunotherapy, including the use of cancer vaccines, such as autologous vaccines, is effective for cancer patients with tumor burdens of less than $10^8$ tumor cells. Immunotherapy is often used as an adjunctive therapy in combination with other therapies such as surgery, radiation therapy and chemotherapy to clear out the remaining tumor cells. Immunotherapy and the use of tumor vaccines have not proven effective against a tumor burden greater than $5 \times 10^9$ to $10^{11}$ tumor cells, which is typical in a patient with small, symptomatic metastases. In addition, autologous tumor vaccination involves complicated procedures and requires a tumor specimen be processed for each patient to be treated.

Alcohol intratumoral injection therapy has been applied in clinical practices in the treatment of liver neoplasms and others cancers. Alcohol injection therapy alone does not kill all tumor cells because of the limiting volume of alcohol that can be injected, coagulating necrosis of normal living tissues caused by alcohol, alcohol dilution by the blood in the tumor to non-effective concentrations, especially when treating the large tumors and other factors. Alcohol cannot be injected close to critical structures, such as the central nervous system. Alcohol intratumoral injection therapy also has been administered with certain anti-tumor agents that are co-injected (Yu et al. (1994) *J. Current Oncology*, 1:97-100). In these protocols, the coagulated mass of tissue resulting from the alcohol injection serves as a slow release depot for the anti-tumor agent.

At present, there is no effective treatment for patients with high tumor burdens. Since early stage tumors are not easily detectable, many patients who are diagnosed with cancer are at the later stages of cancer with the tumor burden greater than $5 \times 10^9$ to $10^{11}$ tumor cells, or the tumor has already metastasized into other tissues. For these patients, traditional cancer therapies such as surgery, radiation therapy and chemotherapy may no longer be effective and/or suitable.

Despite some progress of cancer therapy, there are few, if any, effective treatments. Due to the severity and breadth of neoplasm, tumor and cancer, there is a great need for effective treatments of such diseases or disorders. An ideal cancer therapy should have the potency to eradicate systemic tumor at multiple sites in the body and the specificity to discriminate between neoplastic and non-neoplastic cells. Therefore, it is an object herein to provide treatments for such diseases and disorders. In particular, it is an object herein to provide a cancer therapy that has the potency to eradicate systemic tumor at multiple sites in the body and the specificity to discriminate between neoplastic and non-neoplastic cells.

DISCLOSURE OF THE INVENTION

Provided herein are combinations for intratumoral therapy that include agents that cause coagulation of tumor tissue and agents that enhance the inflammatory response to the resulting coagulated tissue mass. Preferred among the combinations are those that include three components (designated three in one or TIO) for intratumoral injection therapy and methods of treatment using the compositions. The combinations include an oxidizing agent or a reducing agent, a protein denaturing agent or other coagulating means or treatment, and a hapten. The combinations are used to treat tumors, e.g., solid tumors.

It is shown herein that these combinations, such as those that include one or more oxidizing agents and/or reducing agents, protein denaturing agents and haptens have broad applicability in the treatment of various types of neoplasms, tumors and cancers, particularly solid tumors that are not effectively treatable with traditional cancer therapy such as surgery, radiation therapy, chemotherapy and immunotherapy.

Provided herein are methods and compositions for treating neoplasms, tumors and cancers. Encompassed within the methods are the uses of any combinations of one or more oxidizing agents or reducing agents, protein denaturing agents and haptens that can alleviate, reduce, ameliorate, or prevent neoplasms, tumors and cancers; or place or maintain in a state of remission of clinical symptoms or diagnostic markers associated with such neoplasms, tumors and cancers, particularly solid tumors that are not effectively treatable with traditional cancer therapy such as surgery, radiation therapy, chemotherapy and immunotherapy. The combinations can be used alone or in conjunction with other treatments for neoplasms, tumors and cancers.

The neoplasms, tumors and cancers that can be treated include, but are not limited to, the neoplasm of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm. Preferably, the neoplasms, tumors and cancers to be treated is a solid tumor. The combinations are particularly effective for solid tumors, including solid tumor larger than $10^8$ cells, e.g., from about $5 \times 10^9$ to about $10^{11}$ cells.

The combinations are provided to improve the therapeutic efficiencies of cancer therapy for most cancer patients, including very earlier stage cancer patients with visible tumor mass who may not be candidates for surgery and late stage cancer patients with larger tumors or metastases for whom the opportunity for surgery may have passed.

Each component may be a separate composition or agent or may be combined. The combination is intended to induce coagulation of the tumor and to enhance the inflammatory response to the coagulated tissue.

Hence, provided herein are combinations, preferably in the form of pharmaceutical compositions, including one or more oxidizing agents or reducing agents, protein denaturing agents and haptens. The combinations are typically pharmaceutical compositions that include an oxidizing agent or reducing agent, a protein denaturing agent and a hapten formulated for single dosage administration. The compound and agent can be administered separately, such as successively, or can be administered intermittently, or together as three separate compositions as a mixture in a single composition. When administered successively or intermittently, the time period between administration of each is typically on the order of less than a day, preferably less than an hour, but may be longer. The precise order and timing of administration can be determined empirically.

The dosage of each can be empirically determined, but is generally the dosage of an agent normally used to treat neoplasms, tumors and cancers, and an amount sufficient to further enhance other neoplasm treatment, or sufficient when used alone to reduce or ameliorate or in some manner reduce symptoms of the neoplasms. The combinations can be packaged as kits.

The compositions are administered directly into a tumor. Upon administration they result in coagulation of the tumor and create what is herein referred to as an intratumoral autologous drug release biomaterials depot. These biomaterials depots are called IAWBDs.

Immunologic adjuvants can also be administered with the combinations. Such adjuvants include, but are not limited to, Bacille Calmette-Guerin (BCG), interferons or the colony-stimulating factor GM-CSF after the pretreatment with low dose cyclophosphamide.

When the combination TIO is administered to form an IAWBD, the therapy immediately kills a lot of tumor cells by an over-dose oxidation (or reduction) of the tumor matrix and tumor tissue, which results in the shrinking of the tumor. This results in a lower tumor burden that is treatable with immunotherapy or treatment with tumor vaccines. It also creates an area of inflammation that attracts lymphocytes and other inflammatory response mediators to the target tumor site. The attracted lymphocytes include the tumor antigen presenting cells (APCs), macrophages, dendritic cells (DCs), and activated B cells. These lymphocytes are exposed to tumor antigens generated from the tumor cell lysis and elicit a tumor-specific immune response.

When the TIO makes an IAWBD with inflammation and tumor cell lyses, the lysed tumor cells in the resulting depot are modified with the haptens and generate modified, MHC-associated peptides with more complex immunogens, which are then released, and function as an autologous tumor vaccine. Such a tumor vaccine enhances the patient's own tumor immunogenicity, stimulates T lymphocytes against the live tumor cells in and around the original tumor that are not killed by the initial coagulation, metastasized tumor and micro-lesions of tumor after the intratumoral coagulation therapy. This autologous tumor vaccination plays an important role for prevention of the tumor metastases and recovery from the original tumor.

In addition, additional therapeutic viruses or nucleic acids, e.g., DNA, cDNA, can also be included in the combination. Upon administration these will be encapsulated in the IAWBD and can be fused to or transfected into some of the remaining tumor cells in and around the IAWBD, producing in situ genetically modified tumor vaccines and hybrid vaccines. The tumor DNA or RNA from tumor lysis may be transfected into dendritic cells, which directly accept tumor antigen signals. The chemically and genetically modified intratumoral tumor vaccines cooperate to initiate effective antigen-specific and antigen-non-specific or co-stimulatory signal antitumor immunoresponses.

The combinations can also include other agents, such as anti-angiogenic agents, radiosensitizers and other cancer therapeutics. For example, upon administration of a TIO combination that additionally includes other such agents, the resulting coagulum (IAWBD) will slowly release anticancer drugs killing tumor cells not killed by the initial coagulation around original tumor site. The IAWBD can also slowly release radiosensitizer around tumor to increase the radiotherapy efficiency when it is needed. The IAWBD can further slowly release an anti-angiogenic agent to inhibit the blood microvessel formation for new tumor growth.

The anti-neoplastic (anti-cancer) agents used in the combinations and methods include, but are not limited to, an anti-angiogenic agent, an alkylating agent, an antimetabolite, a natural product, a platinum coordination complex, an anthracenedione, a substituted urea, a methylhydrazine derivative, an adrenocortical suppressant, a hormone and an antagonist, an oncogene inhibitor such as an anti-oncogene antibody or an anti-oncogene antisense oligonucleotide, an anti-cancer polysaccharide, or herb extracts such as Chinese herb extracts.

Anti-angiogenic agents include, but are not limited to, an inhibitor of basement membrane degradation, an inhibitor of cell migration, an inhibitor of endothelial cell proliferation, an inhibitor of three-dimensional organization and establishment of potency, an angiostatic gene, an angiostatic chemokine gene, AGM-1470 (TNP-470), angiostatic steroids, angiostatin, antibodies against avβ3, antibodies against bFGF, antibodies against IL-1, antibodies against TNF-α, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, gelatinase inhibitor, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-1 2, laminin, levamisole, linomide, LM609, matrix metalloproteinase inhibitor, marimastat (BB-2516), medroxyprogesterone, 6-methylmercaptopurine riboside, metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4 (PF4), prednisolone, prolactin (16-Kda fragment), proliferin-related protein, prostaglandin synthase inhibitor, protamine, retinoids, Roquinimex (LS-2616. linomide), somatostatin, stromelysin inhibitor, substance P, suramin, SU101, tecogalan sodium (DS-4152), tetrahydrocortisol-sthrombospondins (TSPs), tissue inhibitor of metalloproteinases (TIMP 1, 2, 3), vascular endothelial growth factor inhibitors, vitamin A, Vitaxin and vitreous fluids.

In one embodiment, the combination contains a single composition containing one or more oxidizing agents and/or reducing agents, protein denaturing agents and haptens formulated for injectable delivery or three compositions, one containing an oxidizing agent or reducing agent, another one containing a protein denaturing agent and still another one containing a hapten, where each is in a pharmaceutically acceptable carrier or excipient in an injectable form. Specific therapeutic regimens, pharmaceutical compositions, and kits are also provided.

In a specific embodiment, a combination is provided, which combination comprises: a) a protein denaturing agent; and b) an anti-neoplastic (anti-cancer) agent, such as Ara-C, wherein the protein denaturing agent is not an alcohol or ethanol. In addition, a combination is provided, which combination comprises: a) an oxidizing agent or a reducing agent; b) a protein denaturing agent; and c) an anti-neoplastic (anti-cancer) agent, such as Ara-C.

In another specific embodiment, a combination is provided, which combination comprises: a) an oxidizing agent or a reducing agent; and b) an anti-neoplastic (anti-cancer) agent, such as Ara-C.

In still another specific embodiment, a combination is provided, which combination comprises: a) a hapten; and b) a protein denaturing agent.

In yet another specific embodiment, a combination is provided, which combination comprises: a) a hapten; and b) an oxidizing agent or a reducing agent.

In yet another specific embodiment, a combination is provided, wherein the coagulation agent comprises carbamide peroxide ($CH_6N_2O_3$) and/or a chitosan. Any suitable chitosan can be used. For example, a chitosan oligosaccharide or a water soluble chitosan can be used.

Other names for carbamide peroxide may include urea hydrogen peroxide, Debrox, Exterol, Gly-Oxide, Hyperol and Ortizon. Carbamide peroxide can be prepared by any suitable methods (See e.g., The Merck Index, 13th Ed. 2001 at page 298).

Chitin $(C_8H_{13}NO_5)n$ are cellulose-like biopolymer consisting predominantly of unbranched chains of β-(1→4)-2-acetamido-2-deoxy-D-glucose (also named N-acetyl-D-glucose-amine) residues. A chitosan is a deacylated chitin. Chitosan can be prepared by any suitable methods (See e.g., The Merck Index, 13th Ed. 2001 at pages 353-354; and U.S. Pat. Nos. 6,806,260, 6,780,851, 6,780,822, 6,719,961, 6,716, 970, 6,599,888, 6,521,268, 6,492,350, 6,485,946, 6,465,626 and 6,310,188).

When carbamide peroxide and/or a chitosan is used as the coagulation agent, the hapten can be any suitable hapten such as trinitrophenol (TNP), drinitrophenyl (DNP), N-iodoacetyl-N'-(5-sulfonic 1-naphtyl) ethylene diamine (AED), dinitrofluorobenzene(DNFB) and Ovabulin (OVA).

Also provided is a method for treating neoplasm, in particular solid tumors, in a mammal preferably a human, comprising in situ administration of an effective amount of a hapten and coagulation agent(s) or treatment(s) that causes coagulation of the neoplasm, whereby an autologous immune response is generated against the neoplasm and the neoplasm is treated. The autologous immune response generated against the neoplasm can be a humoral and/or a cellular immune response.

In yet another specific embodiment, a method is provided, wherein the coagulation agent comprises carbamide peroxide ($CH_6N_2O_3$) and/or a chitosan. Any suitable chitosan can be used. For example, a chitosan oligosaccharide or a water soluble chitosan can be used. When carbamide peroxide and/or a chitosan is used as the coagulation agent, the hapten can be any suitable hapten such as trinitrophenol (TNP), drinitrophenyl (DNP), N-iodoacetyl-N'-(5-sulfonic 1-naphtyl) ethylene diamine (AED), dinitrofluorobenzene(DNFB) and Ovabulin (OVA).

Haptens used in the treatment include, but are not limited to, trinitrophenol (TNP), dinitrophenol (DNP), N-iodoacetyl-N'-(5-sulfonic 1-naphtyl) ethylene diamine (AED), dinitrofluorobenzene(DNFB) and Ovabulin (OVA).

Oxidizing agents used in the methods and combinations, include, but are not limited to, hydrogen peroxide ($H_2O_2$), ozone, polyatomic oxygen $O_7$, polyatomic oxygen $O_8$, $NaIO_4$, potassium peroxymonosulfate (oxone), D,L-S-methyllipoic acid methyl ester, tertiary butyl hydroperoxide, menadione, diamide, iodogen, N-bromosuccinimide, omeprazole and N-ethylmaleimide.

Reducing agents used in the combinations and methods include, but are not limited to, hematoxylin, a hypoxic reducing agent such as a nitroimidazole, and nonnitro compound SR 4233.

Protein denaturing agents used in the combinations and treatment include, but are not limited to, an alcohol, guanidine hydrochloride, guanidinium thiocyanate, sodium citrate, 2-mercaptoethanol, sarcosyl, phenol, chloroform and urea. Exemplary alcohols include, but are not limited to, methyl, ethyl, n-propyl, n-butyl, n-pentyl, n-hexyl, n-heptyl, n-octyl, n-decyl, n-dodecyl, n-tetradecyl, n-hexadecyl, n-octadecyl, isopropyl, isobutyl, sec-butyl, tert-butyl, isopentyl, active-amyl, tert-pentyl, cyclopentanol, cyclohexanol, allyl, crotyl, methylvinylmethanol, benzyl, α-phenylethyl, β-phenylethyl, diphenylmethanol, triphenylmethanol, cinnamyl, 1,2-ethanediol, 1,2-propanediol, 1,3-propanediol, glycerol and pentaerythritol alcohol.

Preferably, the combination also includes a facilitating agent and method further comprises administering a facilitating agent that facilitates conjugation between the hapten and a tumor antigen of the neoplasm. The facilitating agents include, but are not limited to, a chelator such as glycyltyrosyl-(N-e-diethylenetri-aminepetaacetic acid)-lysine (GYK-DTPA) or doxorubicin adipic-dihydrazide (ADR-ADH), or a chemical linking agent such as carbodiimide.

Also preferably, the combination also includes an immune response potentiator, and the methods further comprise administering an immune response potentiator to the neoplasm. The immune response potentiators include, but are not limited to, polysaccharides, herb extracts such as Chinese herb extracts, Bacille Calmette-Guerin (BCG), Corynebacterium Parvum, an enzyme such as Vibrio cholera neuraminidase (VCN), Papain, β-Gal and ConA, and a non-virulent virus such as a non-virulent Newcastle virus. Nucleic acids encoding oncogenes or the encoded gene product can also be administered, or be included in the combination of coagulation agents, to enhance the immune response. Exemplary oncogenes include, but are not limited to, abl, erbA, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

The combinations may also include a coagulation lysing agent and the method further comprises administering such agent to the neoplasm, either separately or as part of the combination. Coagulation lysing agents include, but are not limited to, proteinase K, Glycosyl-phosphatidylinositol-B7 and pancreatin.

These combinations and methods can also be administered concurrently, successively or otherwise in conjunction with chemotherapy, e.g., by further including an anti-neoplasm agent in the combination of coagulation agents or administering a combination provided herein, and, then, preferably within the same day, week or other cycle, administering chemotherapy.

The presently contemplated methods can also be used in conjunction with gene therapy, e.g., by further including a tumor suppressor gene, such as p16, p21, p27, p53, RB, WT-1, DCC, NF-1 and APC, in the combination of coagulation agents. Preferably, the tumor suppressor gene is carried out in a viral vector such as an adenovirus vector, a simian virus vector and a conditionally replicating human immunodeficiency viral vector.

In a preferred embodiment, a particular combination of $H_2O_2$ as the oxidizing agent, ethanol as the protein denaturing agent and TNP as the hapten is used in the treatment.

In another preferred embodiment, the oxidizing agent or reducing agent used is from about 0.01% (w/w) to about 35% (w/w), the protein denaturing agent used is from about 1% (w/w) to about 98% (w/w) and the hapten used is from about 1 mg/ml to about 80 mg/ml.

The coagulation can also be achieved by treating the neoplasm with certain physical treatment such as cryotherapy, laser coagulation (ILC), percutaneous microwave coagulation therapy, radio-frequency-induced coagulation necrosis, transpupillary thermotherapy and radiationtherapy.

In a preferred embodiment, the hapten and the coagulation agent(s) are administered to the neoplasm via injection.

In a preferred embodiment, the hapten and the coagulation agent(s) are administered to the neoplasm in combination with a surgical procedure.

Further provided is a method for treating neoplasm, in particular solid tumors, in a mammal preferably a human, comprising in situ administration of an effective amount of an anti-neoplastic (anti-cancer) agent, such as Ara-C, and coagulation agent(s) or treatment(s) that causes coagulation of the neoplasm, whereby the neoplasm is treated. Preferably, the coagulation agent(s) is a protein denaturing agent that is not an alcohol or ethanol. Also preferably, the coagulation agent(s) is a combination of a protein denaturing agent and an oxidizing agent or a reducing agent.

In another specific embodiment, a method is provided for treating neoplasm, in particular solid tumors, in a mammal preferably a human, which method comprises in situ administration of an effective amount of an anti-neoplastic (anti-cancer) agent, such as Ara-C, and an oxidizing agent or a reducing agent that causes coagulation of the neoplasm, whereby the neoplasm is treated.

In still another specific embodiment, a method is provided for treating neoplasm, in particular solid tumors, in a mammal preferably a human, which method comprises in situ administration of an effective amount of a hapten and a protein denaturing agent, whereby an autologous immune response is generated against the neoplasm and the neoplasm is treated.

In yet another specific embodiment, a method is provided for treating neoplasm, in particular solid tumors, in a mammal preferably a human, which method comprises in situ administration of an effective amount of a hapten and an oxidizing agent or a reducing agent, whereby an autologous immune response is generated against the neoplasm and the neoplasm is treated.

Particular compositions of and combinations are described in the sections and subsections which follow.

MODES OF CARRYING OUT THE INVENTION

Figure 1:
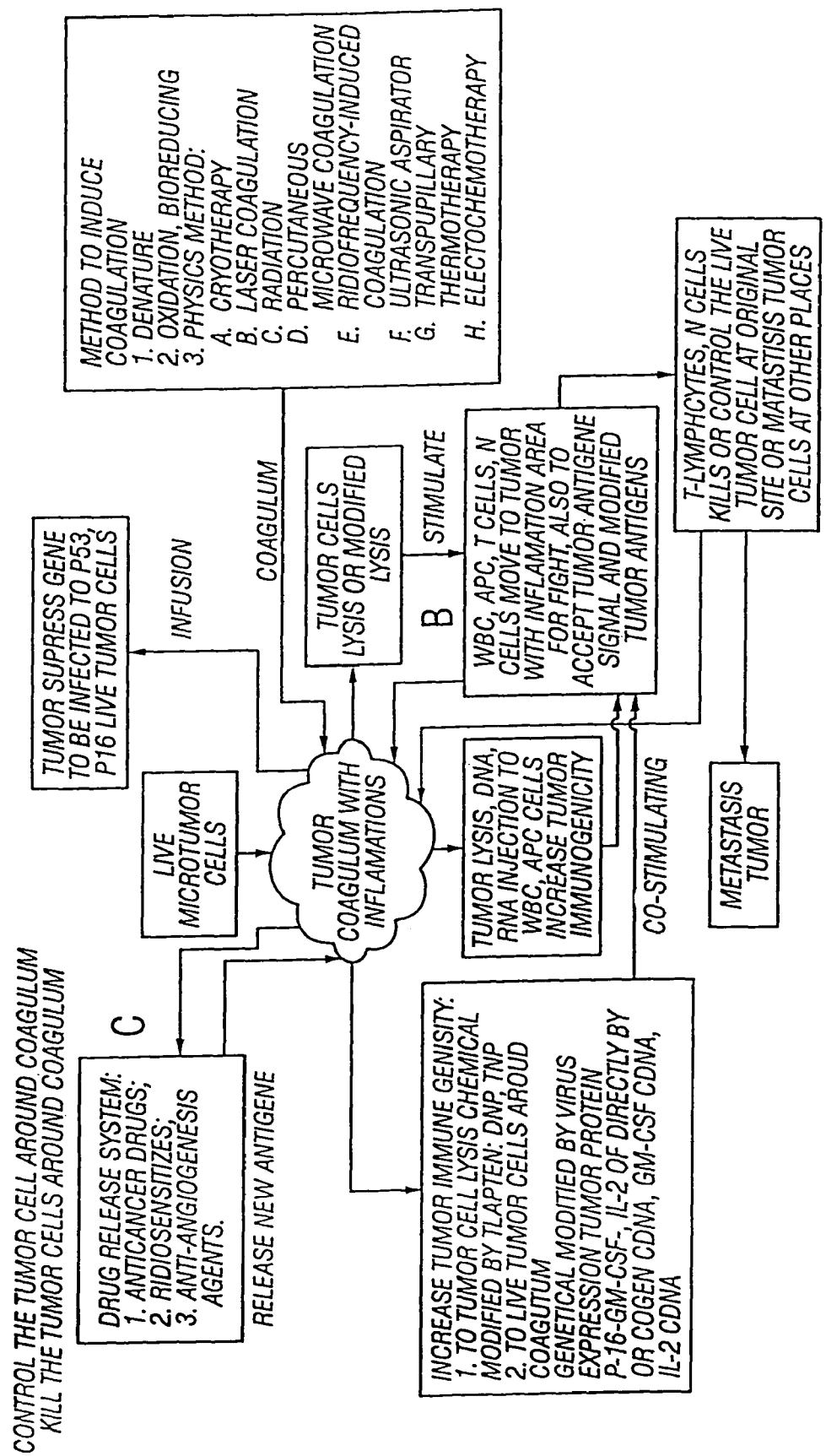
FIG. 1 depicts the general concept and certain embodiments of the disclosed neoplasm treatment methods.
Figure 2:
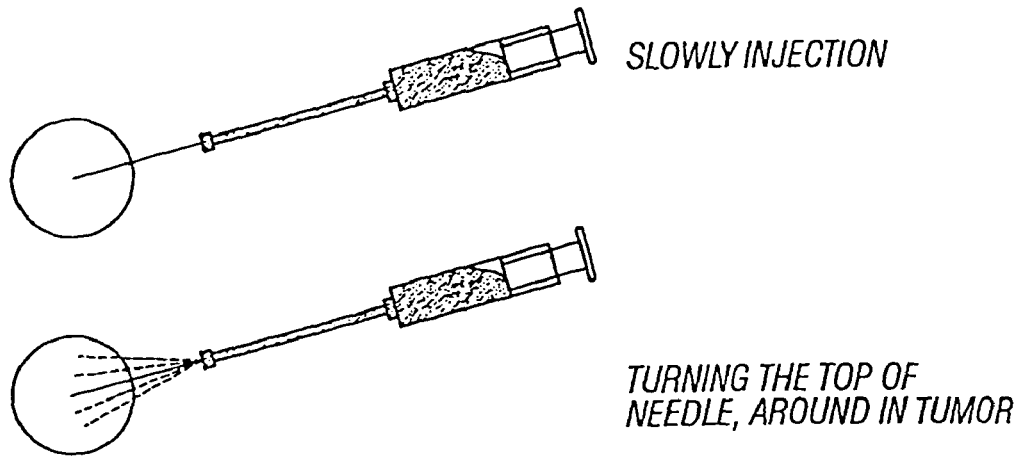
FIG. 2 illustrates certain apparatus and methods for injection of the disclosed combination into tumors.
Figure 2:
Figure 2:

Provided herein are combinations and methods for intratumoral cancer immunotherapy involving coagulation of neoplasm, tumor and cancer tissues, and preferably combined with intratumoral, focused chemotherapy, gene therapy, radiotherapy and surgery. It is disclosed herein that coagulation of neoplasm, tumor or cancer tissues and cells in conjunction with in situ delivery of a hapten is an effective treatment for such neoplasm, tumor or cancer. Coagulation can be achieved by chemical means, i.e., treating the neoplasm tissues or cells with a combination of an oxidizing agent or a reducing agent and a protein denaturing agent. Coagulation can also be achieved by physical means, i.e., subjecting the neoplasm tissues and cells to various physical treatment such as cryotherapy, laser coagulation (ILC), percutaneous microwave coagulation therapy, radio-frequency-induced coagulation necrosis, transpupillary thermotherapy and radiationtherapy.

Although not wished to be bound by any theories or mechanisms described herein, it is the current understanding that the following effects of coagulation and hapten contribute to the treatment of neoplasms, tumors and cancers. First, coagulation of the neoplasm tissues and cells, whether mediated by in situ chemical or physical means, kills at least some, in many cases more than 50% of the neoplastic cells in a target tumor. In general, the coagulation acts like a surgery that reduces the neoplasm mass burden to be treated by the subsequent immunotherapy. In addition, coagulation also results in structural changes in the cell surface, the extracellular matrix and cell lysis to release the contents of the neoplastic cells, i.e., local inflammation. This inflammatory effect, coupled with the presence of the added hapten, which is combined with the tumor-specific antigen due to neoplastic cell lysis by coagulation, further generates more complex immunogens. This inflammatory area attracts various lymphocytes, such as the tumor antigen presenting cells (APCs), macrophages, dendritic cells (DCs) and activated B cells, to the area and interacts with the tumor antigens, e.g., the complex tumor antigens, DNAs, RNAs and other contents released from the cell lysis. These interactions induce a tumor-specific immune response, which includes humoral, cellular and complement-mediated response. This local tumor-specific immune response is further enhanced by the presence of adjacent live neoplastic cells not initially killed by the coagulation. In this way, the subsequent tumor-specific immune response augments the effect of the coagulation (in situ vaccination) and extends to the metastasized neoplastic sites as an "invisible surgical knife" preventing recurrence and metastasis of the neoplastic cells.

The present combinations and methods may also exert their therapeutic effects through their effects on extracellular matrix (EM). In vivo, tumor cells are surrounded by the extracellular matrix (EM) such as collagen, fibronectin, proteoglycans (protein/Carbohydrate), hyaluronic acid and other high molecular weight substances. It has been shown that there are differences between the EM of tumor and that of normal tissues. Fibronectins and collagens, the two major EM components that are mostly studied, are both qualitatively and quantitatively altered with transformation of cells. Research has shown that fibronectin secreted by transformed cells is phosphorylated to a much greater extent when compared to equivalent normal tissues. In addition, the fibronectin synthesized by tumor cells has a slow electrophoretic mobility. The tumor cells also have very little, if any, surface-associated fibronectin. The amount of secreted fibronectin by tumor cells is much lower than that secreted by normal cells. Collagen is a long protein strand or molecular rope which binds other substances together and acts as a carrier of information to the cells. It was shown that the nature of the collagen surrounding cells is related to cell shape, differentiation and cell division. It is believed that the modification or destruction of the EM of cancer results in the starvation of the cells, shutting off critically needed glucose to cancer cells.

When the present combination, e.g., the combinations described in the Disclosure of the Invention or the combinations described in the following Section B, is injected into tumor, the combination will be distributed throughout the EM surrounding the tumor. The EM will be denatured or altered by oxidation or reduction. For example, when hydrogen peroxide ($H_2O_2$) is used as the oxidizing agent, EM will at least be partially destroyed by the hydrogen peroxide to produce the hydroxyl radicals (305 nm light). EM will also at least be partially destroyed by the reactions with a reducing agent such as hematoxylin. Such partial destruction will result in the EM shape disfiguring. In addition, when an anticancer drug is used in conjunction with the present combination, the anticancer drug will be trapped to some extent in collagen and other EM substances. Subsequent to EM changes, the central portion of the tumor is necrosed while the periphery is only slightly modified, which allows slow release of anti-cancer drug to surrounding tumor cells after the initial therapy. Further, while the tumor is necrosed, a lot of tumor proteins can be modified by a hapten, such as TNP or DNP if included in the present combination, to increase the tumor-specific antigenecity.

The tumor-specific immune response can be augmented by in situ administering or by including in the combination of coagulation agents, a facilitating agent that facilitates conjugation between the hapten and a tumor antigen, an immune response potentiator, a coagulation lysing agent, an oncogene product or any combination thereof.

The contemplated treatment can be used alone or can be used in conjunction with other cancer therapies, such as, but are not limited to, surgery, radiation therapy, chemotherapy and traditional immunotherapy. For example, this treatment can be used with chemotherapy by including an anti-neoplastic agent, such as an anti-angiogenic agent, in the combination of coagulation agents. This combination treatment is advantageous because coagulation enhances retention of the anti-neoplastic agents within the coagulated neoplastic mass, thereby exposing the neoplastic mass to the anti-neoplasm agent for longer time. In this aspect, coagulation acts as a controlled drug-release vehicle.

In summary, the coagulation eliminates at least some or more than 50% of the neoplastic cells in the target tumor. Anti-neoplastic agents kill the left-over live neoplastic cells not initially killed by the coagulation. The in situ "vaccination" further eliminates live neoplastic cells, resulting in better therapeutic efficacy than any of the separate treatments.

In one example, the treatment can be used with radiation-therapy by including a radiation sensitizer in the combination of coagulation agents. In this aspect, the coagulation acts as controlled drug release vehicle to release the radiation sensitizer to the live neoplastic cells not initially killed by the coagulation and increases radiation therapy efficacy.

In another example, the treatment can be used before surgery. In this aspect, coagulation plays an important role for the pretreatment of neoplasm and makes it easier for surgeon to remove the neoplastic mass and reduces the neoplasm metastasis rate.

In still another example, the treatment can be used with gene therapy by including nucleic acid encoding a desired wild-type oncogene, tumor suppressor gene, immune cytokine gene or apoptosis gene in the combination of coagulation agents. This combination treatment is advantageous because coagulation may facilitate the delivery of these wild-type oncogenes or tumor suppressor genes into live neoplastic cells, which may then be carried to other sites. In this aspect, the live neoplastic cells affected by coagulation act as gene therapy vectors.

In all treatments, an immunological adjuvant, such as BCG, can be used in the combination of coagulation agents to augment the immune response to the tumor cells. The immunological adjuvants can be reinjected repeatedly, e.g., every 2 to 4 weeks. Low-dose, e.g., 200 to 300 mg/m$^2$ cyclosphamide can also be administered prior to, e.g., 3 days, each in situ vaccination to augment the development of cell-mediated immunity to the antigens.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, an oxidation-reduction reaction refers to a reaction in which electrons are transferred from a donor to an acceptor molecule.

As used herein, an oxidizing agent (or oxidant) refers to an agent that accepts electrons in an oxidation-reduction reaction.

As used herein, a reducing agent (or reductant) refers to an agent that donates electrons in an oxidation-reduction reaction.

As used herein, a protein denaturing agent refers to an agent that causes the denaturation of the protein, i.e., partial or complete unfolding of the specific native conformation (secondary, tertiary or quaternary structure) of the polypeptide chain(s) of the protein.

As used herein, alcohol refers to a series of hydroxyl compounds having the general structure formula $C_nH_{2n+1}$, including methanol and ethanol.

As used herein, hapten refers to an antibody-specific substance that cannot induce antibody formation unless bound to a carrier or molecules. Once a hapten is conjugated to a carrier/molecule, the antibody produced using the conjugate may recognize the hapten and/or the carrier/portion. The conjugate of hapten-carrier/molecule may also generate specific cellular immune response.

As used herein, an anti-neoplastic treatment refers to any treatment designed to treat the neoplasm, tumor or cancer by lessening or ameliorating its symptoms. Treatments that prevent the occurrence of neoplasm, tumor or cancer or lessen its severity are also contemplated.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, malignant, as applies to tumors, refers to primary tumors that have the capacity of metastasis with loss of both growth control and positional control.

As used herein, an anti-neoplasm agent (used interchangeably with anti-neoplastic agent, anti-tumor or anti-cancer agent) refers to any agents used in the anti-neoplasm treatment. These include any agents, that when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein. Anti-neoplastic agents include, but are not limited to, anti-angiogenic agents, alkylating agents, antimetabolite, certain natural products, platinum coordination complexes, anthracenediones, substituted ureas, methylhydrazine derivatives, adrenocortical suppressants, certain hormones and antagonists, anti-cancer polysaccharides and certain herb extracts such as Chinese herb extracts.

As used herein, anti-neoplasm agent (or anti-tumor or anti-cancer agent) or anti-neoplasm treatment does not encompass a combination comprising an oxidizing agent or a reducing agent, a protein denaturing agent; and a hapten, or use thereof for treatment, but encompasses all agents and treatment modalities known to those of skill in the art to ameliorate the symptoms in some manner of a neoplasm, tumor or cancer.

As used herein, "angiogenesis" refers to the generation of new blood vessels from parent microvessels. Angiogenesis is highly regulated by a system of angiogenic stimulators and inhibitors. Pathological angiogenesis is caused by a shift in the net balance between stimulators and inhibitors of angiogenesis, e.g., due to the overproduction of normal or aberrant forms of angiogenic mediators, or due to a relative deficiency in inhibitors of this process.

As used herein, "undesired and/or uncontrolled angiogenesis" refers to pathological angiogenesis wherein the influence of angiogenesis stimulators outweighs the influence of angiogenesis inhibitors.

As used herein, "anti-angiogenic treatment or agent" refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. As used herein, "inhibitor of an endotheliase" is not considered an "anti-angiogenic treatment or agent."

As used herein, "tumor suppressor gene" (or anti-oncogene, cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wilm's tumor), DCC (deleted in colonic carcinoma), NF-1 (neurofibrosarcoma) and APC (adenomatous polypopsis coli).

As used herein, "oncogene" refers to a mutated and/or overexpressed version of a normal gene of animal cells (the proto-oncogene) that in a dominant fashion can release the cell from normal restraints on growth, and thus alone, or in concert with other changes, convert a cell into a tumor cell. Exemplary oncogenes include, but are not limited to, abl, erbA, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

As used herein, "antisense polynucleotides" refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand.

As used herein, antibody includes antibody fragments, such as Fab fragments, which are composed of a light chain and the variable region of a heavy chain.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "a facilitating agent that facilitates conjugation between the hapten and a tumor antigen" refers to an agent that links the hapten to the tumor antigen, or any agent that facilitates such linkage. The linkage between the hapten and the tumor antigen can be covalent or non-covalent, and can be mediated by hydrophobic, polar, ionic, electrostatic or other interactions.

As used herein, "immune response" refers to alteration in the reactivity of an organism's immune system in response to an antigen; in vertebrates, this may involve antibody production, induction of cell-mediated immunity, complement activation or development of immunological tolerance.

As used herein, "immune response potentiator" refers to a substance that enhances an antigen's effect in eliciting an immune response.

As used herein, "coagulation" refers to a process of causing transformation of cells, contents therein, and extracellular matrix into a soft, semisolid or solid mass.

As used herein, "coagulation lysing agent" refers to an agent that loosens or solubilize the coagulation.

As used herein, "coagulation of neoplasm" refers to a process of causing transformation of neoplastic cells, contents therein, and extracellular matrix into a soft, semisolid or solid mass, which transformation results in death of the coagulated neoplastic cells and enhance the coagulated neoplastic cells' retention of agents administered to the neoplasm.

As used herein, a cytokine is a factor, such as lymphokine or monokine, that is produced by cells that affect the same or other cells. A "cytokine" is one of the group of molecules involved in signaling between cells during immune responses. Cytokines are proteins or peptides; and some are glycoproteins.

As used herein, "interleukin (IL)" refers to a large group of cytokines produced mainly by T cells, although some are also produced by mononuclear phagocytes, or by tissue cells. They have a variety of functions, but most of them are involved in directing other cells to divide and differentiate. Each interleukin acts on specific, limited group of cells which express the correct receptors for that cytokine.

As used herein, "interleukin-1 (IL-1)" refers to interleukins made by certain antigen presenting cells (APCs) that, along with IL-6, act as co-stimulatory signals for T cell activation. The IL-1 gene family includes IL-1α, IL-1β and IL-1 receptor antagonist (IL-IRa) (Dinarello, *Eur. Cytokine Netw.*, 5(6):517-522 (1994)). Each member is first synthesized as a precursor protein; the precursors for IL-1 (proIL-1α and proIL-1β) have molecular weights of about 31,000 Da. The proIL-1α and mature 17,000 Da IL-1α are both biologically active whereas the proIL-1β requires cleavage to a 17,000 Da peptide for optimal biological activity. The IL-IRa precursor has a leader sequence and is cleaved to its mature form and secreted like most proteins. IL-1α and IL-1β are potent agonists where IL-1Ra is a specific receptor antagonist. Moreover, IL-IRa appears to be a pure receptor antagonist with no agonist activity in vitro or in vivo. Although IL-1Ra is a secreted protein, there is another form of this molecule which is retained inside cells. It is called "intracellular" (ic) IL-1Ra. IcIL-1Ra results from alternate mRNA splice insertion of the IL-I Ra gene replacing the exon coding for the signal peptide. The IL-1Ra forms are functionally indistinguishable.

Thus, reference, for example, to "IL-1" encompasses all proteins encoded by the IL-1 gene family including IL-1α, IL-1β, IL-1Ra and icIL-1Ra, or an equivalent molecule obtained from any other source or that has been prepared synthetically. It is intended to encompass IL-1 with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e., Watson et al. *Molecular Biology of the Gene*, 4th Edition, 1987, The Bejacmin/Cummings Pub. co., p.224).

Such substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |

TABLE 1-continued

| Original residue | Conservative substitution |
|---|---|
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, the terms "a therapeutic agent", "therapeutic regimen", "radioprotectant", "chemotherapeutic" mean conventional drugs and drug therapies, including vaccines, which are known to those skilled in the art. "Radiotherapeutic" agents are well known in the art.

As used herein, "vaccine" refers to any compositions intended for active immunological prophylaxis. A vaccine may be used therapeutically to treat a disease, or to prevent development of a disease or to decrease the severity of a disease either proactively or after infection. Exemplary vaccines include, but are not limited to, preparations of killed microbes of virulent strains or living microbes of attenuated (variant or mutant) strains, or microbial, fungal, plant, protozoa, or metazoa derivatives or products. "Vaccine" also encompasses protein/peptide and nucleotide based vaccines.

As used herein, "cytotoxic cells" refers to cells that kill virally infected targets expressing antigenic peptides presented by MHC class I molecules.

As used herein, "serum" refers to the fluid portion of the blood obtained after removal of the fibrin clot and blood cells, distinguished from the plasma in circulating blood.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, treatment means any manner in which the symptoms of a conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, eg., Nogrady (1985) *Medicinal Chemistry A Biochemical Approach*, Oxford University Press, New York, pages 388-392).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in in vitro systems designed to test or use such activities. Thus, for purposes herein the biological activity of a luciferase is its oxygenase activity whereby, upon oxidation of a substrate, light is produced.

As used herein, a receptor refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:
a) enzymes: specific transport proteins or enzymes essential to survival of microorganisms, which could serve as targets for antibiotic [ligand] selection;
b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases
c) nucleic acids: identification of ligand, such as protein or RNA, binding sites;
d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];
e) hormone receptors: determination of the ligands that bind with high affinity to a receptor is useful in the development of hormone replacement therapies; for example, identification of ligands that bind to such receptors may lead to the development of drugs to control blood pressure; and
f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions [see, e.g., Table 1, above] that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:
1) high stringency: 0.1×SSPE, 0.1% SDS, 65C
2) medium stringency: 0.2×SSPE, 0.1% SDS, 50C
3) low stringency: 1.0×SSPE, 0.1% SDS, 50C It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, a composition refers to a any mixture. It may be a solution, a suspension, liquid, powder, a paste, aqueous, non-aqueous or any combination thereof.

As used herein, a combination refers to any association between two or among more items. Combinations include compositions in which two or more components are contained in a single mixture; it also includes two separate combinations that are associated.

As used herein, fluid refers to any composition that can flow. Fluids thus encompass compositions that are in the form of semi-solids, pastes, solutions, aqueous mixtures, gels, lotions, creams and other such compositions.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description of the invention is divided into the subsections that follow.

B. Combinations

In a specific embodiment, provided herein is a combination useful for intratumoral therapy, which combination comprises: a) an oxidizing agent and/or a reducing agent; b) a protein denaturing agent; and c) a hapten.

The oxidizing or reducing agent, the protein denaturing agent and the hapten can be formulated in a single pharmaceutical composition or each can be formulated in a separate pharmaceutical composition.

Any oxidizing agent that is bio-tolerable can be used in the combination. In a preferred embodiment, the oxidizing agent used is hydrogen peroxide ($H_2O_2$), ozone ($O_3$), polyatomic oxygen $O_7$, polyatomic oxygen $O_8$, $NaIO_4$, potassium peroxymonosulfate (oxone) (Wozniak et al., *Bioorg. Med. Chem. Lett.*, 8(19):2641-6 (1998)), D,L-S-methyllipoic acid methyl ester (Pan and Jordan, *Biochemistry*, 37(5):1357-64 (1998)), tertiary butyl hydroperoxide (Tarin et al., *Mol. Hum. Reprod.*, 2(12):895-901 (1996)), menadione (Santini et al., *Free Radic. Biol. Med.*, 20(7):915-24 (1996)), diamide (Bosin and Kasper, *J. Biochem. Toxicol.*, 7(3):139-45 (1992)), iodogen (Saha et al., *Int. J. Rad. Appl. Instrum.*, 16(4):431-3 (1989)), N-bromosuccinimide (Sinn et al., *Anal. Biochem.*, 170(1): 186-92 (1988)), omeprazole (Im et al., *J. Biol. Chem.*, 260 (8):4591-7 (1985)), or N-ethylmaleimide (Marzulli et al., *Boll. Soc. Ital. Biol. Sper.*, 61(1):121-7 (1985)).

Any reducing agent that is bio-tolerable can be used in the combination. In a preferred embodiment, the reducing agent used is hematoxylin, a hypoxic reducing agent such as a nitroimidazole, or nonnitro compound tirapazamine (SR-4233) (Zhang and Stevens, *Melanoma Res.*, 8(6):510-5 (1998)).

Any protein denaturing agent that is bio-tolerable can be used in the combination. In a preferred embodiment, the protein denaturing agent used is an alcohol, guanidine hydrochloride (Inouye et al., *J. Clin. Microbiol.*, 20(3):525-9 (1984)), guanidinium thiocyanate, sodium citrate, 2-mercaptoethanol, the ionic detergent sarcosyl (Klekamp and Weil, *Arch. Biochem. Biophys.*, 246(2):783-800 (1986)), phenol, chloroform, urea or an acid. Nonlimiting examples of alcohols that can be used in the combination include methyl, ethyl, n-propyl, n-butyl, n-pentyl, n-hexyl, n-heptyl, n-octyl, n-decyl, n-dodecyl, n-tetradecyl, n-hexadecyl, n-octadecyl, isopropyl, isobutyl, sec-butyl, tert-butyl, isopentyl, active-amyl, tert-pentyl, cyclopentanol, cyclohexanol, allyl, crotyl, methylvinylmethanol, benzyl, α-phenylethyl, β-phenylethyl, diphenylmethanol, triphenylmethanol, cinnamyl, 1,2-ethanediol, 1,2-propanediol, 1,3-propanediol, glycerol or pentaerythritol alcohol. In a more preferred embodiment, the alcohol used is ethanol.

Any hapten that is bio-tolerable can be used in the combination. In a preferred embodiment, the hapten used is trinitrophenol (TNP) (Dieli et al., *Int. Immunol.*, 9(1): 1-8 (1997)), dinitrophenol (DNP) (Stjamkvist et al., *J. Pharm. Sci.*, 80(5): 436-40 (1991)), N-iodoacetyl-N'-(5-sulfonic 1-naphtyl) ethylene diamine (AED) (Mizuochi et al., *J. Immunol.*, 134(2): 673-6 (1985)), dinitrofluorobenzene (DNFB) (Claman, *J. Immunol.*, 116(3):704-9 (1976)) or Ovabulin (OVA) (Katz et al., *J. Immunol.*, 107(5):1319-28 (1971)).

In another specific embodiment, the combination further comprises an anti-neoplasm agent for combined intratumoral therapy and chemotherapy.

Any anti-neoplasm agents can be used in the combination. In a preferred embodiment, the anti-neoplasm agent used is an anti-angiogenic agent. More preferably, the anti-angiogenic agent is an inhibitor of basement membrane degradation, an inhibitor of cell migration, an inhibitor of endothelial cell proliferation, an inhibitor of three-dimensional organization and establishment of potency. Examples of such anti-angiogenic agent are further illustrated in the following Table 2 (Auerbach and Auerbach, *Pharmacol. Ther.*, 63)3):265-311 (1994)).

TABLE 2

| Anti-angiogenic agent | | |
|---|---|---|
| Type | Subtypes | Examples |
| Inhibitors of basement membrane degradation | Protease inhibitors | Plasminogen activators (e.g. PAI-1, PAI-2) tissue inhibitors of metalloproteinases (e.g., TIMP-1 and TIMP-2) phenylalanyl-propyl-arginine chloromethyl ketone-thrombin |
| | Cartilage-derived inhibitors Epithelium-derived inhibitors | Cartilage-derived inhibitor (CDI) |

TABLE 2-continued

| Type | Subtypes | Examples |
|---|---|---|
| | Phorbol esters | 1-10-phenanthroline |
| | Steriods | Medroxyprogesterone acetate, dexamethasone, medroxyprogeste-rone, triamcinolone acetonide, proline analogs and trans-retinoic acid, analogues of somatostatin |
| | Antibiotics | minocycline, sulphonated derivatives of distamycin A |
| Inhibitors of cell migration | Taxol, colchicine, vinblastine, nocodazole | Taxol, colchicine, vinblastine, nocodazole |
| | Interferons | Leukocyte ($\alpha/\beta$) IFN |
| | Cholera toxin | |
| | The TGFβ family | |
| | α-Difluoromethyl ornithine and other inhibitors of ornithine decarboxylase | |
| | Inhibitors of FGF: protanine, PF4, suramin | |
| | Corticosteroids and heparin | Hexosaminoglycan sulfate |
| | Interleukin-8 | |
| | SPARC | SPARC ("Secreted Protein, Acidic and Rich in Cysteines") |
| | Inhibitors of platelet-activating factor | *Bothrops jararaca* venon |
| | Targeting mast cells and macrophages: thiols and gold-containing compounds | |
| | Targeting lymphocytes: steroids, anti-lymphocyte sera, irradiation | Cyclosporin opioids such as β-endorphin or morphine sulfate, AGM-1470 |
| | Targeting the extracellular matrix: peptides, antibodies, sulfated chitin derivatives | |
| | Heparin | |
| | Prostaglandins inhibitors | prostaglandin synthesis, like indomethacin and aspirin, ketorolac, mitoxantrone or bisantrene, α-guiaconic acid and their derivatives, amiloride |
| | Placental ribonuclease inhibitor | RNasin, glycine-arginine-glycine-asparagine-serine (GRGDS), actin and an anti-actin antibody inhibit |
| | Antibiotics | herbamycin, bleomycin, eponemycin, erbstatin, radicicol and staurosporine |
| | Other inhibitors of cell migration | Nicardipine, sphingosine-1-phosphate, linomide (N-phenylmethyl-1,2-dihydro-4-hydroxyl-1-methyl-2-oxoquinoline-3-carboxamide), platelet-endothelial cell adhesion molecule-1 (PECAM-1) |
| Inhibitors of endothelial cell proliferation | Inhibitors of fibroblast growth factor | Blocking antibodies to FGF, pentosan polysulfate, heparinase, protamine, somatostatin analogues, such as octreotide |
| | Thrombospondins | TSP1, TSP2 and TSP3 |
| | Phorbol esters | |
| | Retinoids | Etretin, etretinate or isotretinoin, acitretin, genistein |
| | The TGFβs | TGFβ, TGFβ1 and TGFβ2 |
| | Tumor necrosis factor, interfereons, interleukins and other cytokines | TNF, IL-1, IFN-λ, IFN-α and macrophage-derived endothelial cell inhibitor |
| | Steroids and heparin | Tetrahydro S, hydrocortisone, β-cyclodextrin tetradecasulfate, estrogen metabolites such as 2-methoxyoestradiol, steriods were coadministered with DS4152, a bacterially derived sulfated polysaccharide complex |
| | Suramin | Suramin, a polysulfonated urea |
| | $a_2$-Macroglobulin | |
| | Antibodies to growth factors | Antibodies to bFGF, antibodies to peptides of VEGF, hepatocyte growth factor (scatter factor), anti-scatter factor antibodies |

TABLE 2-continued

Anti-angiogenic agent

| Type | Subtypes | Examples |
|---|---|---|
| | Anti-angiogenic peptides | The 16 kDa fragment of prolactin, heparin-binding peptide fragments from fibronectin, selected peptides of TSP, atrial natriuretic polypeptide, PF4, a non-heparin-binding analog of PF4, rPF4-241 |
| | Retina-derived inhibitors | Crude extract of the retina in combination with adult serum |
| | Antibiotics | Rapamycin, eponemycin, the spermidine moiety-containing compound 15-deoxyspergualin, TAN-1120, a baumycin-group anthracycline, d-penicillamine, fumagillin, as well as its more potent synthetic analogue AGM-1470 (TNP-470), FR-111142, which was isolated from strain F-2015 of *Scolecobasiwn arenarium*, WF-16775$A_1$ and $A_2$, isolated from *Chaetasbolisia erysiphoides*, SP-PG (or its most active component, DS-4152), a sulfated polysaccharide-peptidoglycan complex produced by an *Arthobacter* species, tetracyclines, minocycline |
| | Glycosaminoglycans SPARC | Hyaluronan |
| | Other pharmacological agents | Chloroquine, magnosalin, sulfapyridine, several opioids, gold compounds, dimethyl sulfoxide |
| Inhibitors of three-dimensional organization and establishment of potency of new blood vessels | The TGFβs | TGFβ1, TGFβ2 and TGFβ3 |
| | Interferons | IFN-λ, IFN-α |
| | Fatty acids | |
| | Oxazolones | MD 27032 (4-propyl-5(4-pyridinyl-2(3H)-oxazolone) |
| | Inhibitors of basement membrane biosynthesis | Cyclic adenosine monophosphate, cis-hydroxy-proline, an inhibitor of collagen production |
| | Inhibitors of cell adhesion molecules | YSIGR-containing peptides, Arg-Gly-Asp (RGD)-containing peptide Gly-Arg-Gly-Asp-Ser (GRGDS), vitronectin, fibronectin, antibodies, $α_vβ_3$ integrins, antibodies to $α_vβ_3$ inhibit, antibodies to E-selectin, sialyl Lewis-X ligand |
| | Other inhibitors of three-dimensional organization of endothelial cells | Nicardipine, phosphokinase C inhibitors, such as calphostin C and staurosporine, a chimeric toxin in which aFGF was fused to mutant forms of *Pseudomonas* exotoxin, IL-1β, IL-6, TGF-β and platelet-derived growth factor-BB, irsogladine, fenretinide, a proline analog, L-adetine-2-carboxylic acid, cyclosporine, the 16 kDa fragment of prolactin |
| Physiological and physical interventions | Cell-cell interactions | pericyte, endothelial-pericyte interactions, cocultures of cardiac microvascular endothelial cells and ventricular myocytes |
| | Blood flow | |
| | Photodynamic therapy | Photocoagulation of photodynamic therapy |
| | Hyperthermia | The effect of hyperthermia may be exerted by a combination of endothelial cell killing, inhibition of replication, inhibition of cell migration or by a combination of these mechanisms |
| | Hypoxia | |

In another preferred embodiment, the anti-angiogenic agent used is AGM-1470 (TNP-470), angiostatic steroids, angiostatin, antibodies against avβ3, antibodies against bFGF, antibodies against IL-1, antibodies against TNF-α, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, gelatinase inhibitor, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, matrix metalloproteinase inhibitor, marimastat (BB-2516), medroxyprogesterone, 6-methylmercaptopurine riboside, metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4

(PF4), prednisolone, prolactin (16-Kda fragment), proliferin-related protein, prostaglandin synthase inhibitor, protamine, retinoids, Roquinimex (LS-2616. linomide), somatostatin, stromelysin inhibitor, substance P, suramin, SU101, tecogalan sodium (DS-4152), tetrahydrocortisol-sthrombo-spondins (TSPs), tissue inhibitor of metalloproteinases (TIMP 1, 2, 3), vascular endothelial growth factor inhibitors, vitamin A, Vitaxin, vitreous fluids, thalidomide, 3-aminothalidomide, 3-hydroxythalidomide and metabolites or hydrolysis products of thalidomide, 3-aminothalidomide, or 3-hydroxythalidomide (((O'Reilly, *Investigational New Drugs*, 15:5-13 (1997); *J. Nat'l Cancer Instit.*, 88:786-788 (1996); U.S. Pat. Nos. 5,593,990, 5,629,327 and 5,712,291). Also preferably, the anti-angiogenic agent used is an angiostatic gene such as angiostain, endostain, kringle-5, PEX, TIMP-1, TIMP-2, TIMP-3, TIMP-4, endo::angio, or endo::PEX; or an angiostatic chemokine genes such as IP-10, Mig, or SDF-1α.

In still another preferred embodiment, the anti-neoplasm agent used is an alkylating agent, an antimetabolite, a natural product, a platinum coordination complex, an anthracenedione, a substituted urea, a methylhydrazine derivative, an adrenocortical suppressant, a hormone and an antagonist. Examples of such anti-neoplasm agents are further illustrated in the following Table 3:

TABLE 3

Chemotherapeutic Agents Useful in Neoplastic Disease

| CLASS | TYPE OF AGENT | NONPROPRIETARY NAMES | DISEASE* |
|---|---|---|---|
| Alkylating Agents | Nitrogen Mustards | Mechlorethamine | Hodgkin's disease, non-Hodgkin's lymphomas |
| | | Cyclophosphamide | Acute and chronic lymphocytic leukemias, Hodgkin's disease, non-Hodgkin's lymphomas, multiple myeloma, neuroblastoma, breast, ovary, lung, Wilms' tumor, cervix, testes, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimines and Methylmelanines | Hexamethylmelanine | Ovary |
| | | Thiotepa | Bladder, breast, ovary |
| | Alkly Sulfonates | Busulfan | Chronic Granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazenes | Dacarbazine (DTIC; dimethyltriazenoi-midazole-carboxamide) | Malignant melanoma, Hodgkin's disease, soft-tissue sarcomas |
| Antimetabolites | Folic Acid Analogs | Methotrexate (amethopterin) | Acute lymphocytic leukemia, chorio-carcinoma, mycosis fungoides, breast, head and neck, lung, osteogenic sarcoma |
| | Pyrimidine Analogs | Fluorouacil (5-fluorouracil; 5-FU) Floxuridine (fluorode-oxyuridine; FUdR) | Breast, colon, stomach, pancreas, ovary, head and neck, urinary bladder, pre-malignant skin lesions (topical) |
| | | Cytarabine (cytosine arabinoside) | Acute granulocytic and acute lymphocytic leukemias |

TABLE 3-continued

Chemotherapeutic Agents Useful in Neoplastic Disease

| CLASS | TYPE OF AGENT | NONPROPRIETARY NAMES | DISEASE* |
|---|---|---|---|
| | Purine Analogs and Related Inhibitors | Mercaptopurine (6-mercaptopurine; 6-MP) | Acute lymphocytic, acute granulocytic, and chronic granulocytic leukemias |
| | | Thioguanine (6-thioguanine; TG) | Acute granulocytic, acute lymphocytic, and chronic granulocytic leukemias |
| | | Pentostatin (2'-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhab-domyosarcoma, testis, Kaposi sarcoma |
| | | Daunorubicin (daunomycin; rubidomycin) | Acute granulocytic and acute lymphocytic leukemias |
| | | Doxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon-alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methylhydrazine Derivative | Procarbazine (N-methylhydrazine, MIH) | Hodgkin's disease |
| | Adrenocortical Suppressant | Mitotane (o,p'-DDD) | Adrenal cortex |

TABLE 3-continued

Chemotherapeutic Agents Useful in Neoplastic Disease

| CLASS | TYPE OF AGENT | NONPROPRIETARY NAMES | DISEASE* |
|---|---|---|---|
| Hormones and Antagonists | Adrenocorticosteriods | Prednisone (several other equivalent preparations available; see Chapter 59) | Acute and chronic lymphocytic leukemias, non-Hodgkin's lymphomas, Hodgkin's disease, breast |
| | Progestins | Hydroxyprogesterone caproate Medroxyprogestrone acetate Megestrol acetate | Endometrium, breast |
| | Estrogens | Diethylstilbestrol Ethinyl estradiol (other preparations available; see Chapter 57) | Breast prostate |
| | Antiestrogen | Tamoxifen | Breast |
| | Androgens | Testosterone propionate Fluoxymesterone (other preparations available; see Chapter 58) | Breast |
| | Antiandrogen | Flutamide | Prostate |
| | Gonadotropin-Releasing Hormone Analog | Leuprolide | Prostate |

In yet another preferred embodiment, the anti-neoplasm agent used is cytosine analogues such as Cytidine Arabinosyladenine (araC), Daunomycin, Doxorubicin, Methotrexate (MTX); Fluorinated pyrimidines such as 5-Fluorouracil (5-FU); Hydroxyurea; 6-mercaptopurine; plant alkaloids such as vincristine (VCR), VP-16 and vinblastine (VLB); alkylating agent such as Cyclophosphamide tumor cell lyseside, Mesna, Melphalan, BCNU, Cisplatin, Nitrogen Mustard (HN2), Trisamine (HN3); Nonclassic alkylating agent such as Procarbazine; Bleomycin; Mitomycin C; Actinomycin D (DACT); or an enzyme such as L-Asparaginase.

In yet another preferred embodiment, the anti-neoplasm agent used is an oncogene inhibitor. More preferably, the oncogene inhibitor is an anti-oncogene antibody or an anti-oncogene antisense oligonucleotide. For example, antibodies and antisense oligonucleotides against the oncogenes listed in the following Table 4 can be used in the combination.

TABLE 4

Oncogenes and tumor viruses

| Acronym | Virus | Species | Tumor origin | Comments |
|---|---|---|---|---|
| abl | Abelson leukaemia | Mouse | Chronic myelogenous leukaemia | TyrPK(src) |
| erbA | Erythroblastosis | Chicken | | Homology to human glucocorticoid receptor |
| erbB | Erythroblastosis | Chicken | | TryPK EGF/TGFc receptor |
| ets | E26 myeloblastosis | Chicken | | Nuclear |
| fes (fps)[a] | Snyder-Thellen sarcoma Gardner-Arnstein sarcoma | Cat | | TryPK(src) |
| fgr | Gardner-Rasheed sarcoma | Cat | | TyrPK(src) |
| fms | McDonough sarcoma | Cat | | TyrPK CSF-1 receptor |
| fps (fes)[a] | Fujinami sarcoma | Chicken | | TyrPK(src) |
| fos | FBJ osteosarcoma | Mouse | | Nuclear, TR |
| hst | NVT | Human | Stomach tumour | FGF homologue |
| int1 | NVT | Mouse | MMTV-induced carcinoma | Nuclear, TR |
| int2 | NVT | Mouse | MMTV-induced carcinoma | FGF homologue |
| jun | ASV17 sarcoma | Chicken | | Nuclear, TR |
| hit | Hardy-Zuckerman 4 sarcoma | Cat | | TyrPK GFR L |
| B-lym | NVT | Chicken | Bursal lymphoma | |
| mas | NVT | Human | Epidermoiod carcinoma | Potentiates response to angiotensin II |
| met | NVT | Mouse | Osteosarcoma | TyrPK GFR L |
| mil (raf)[b] | Mill Hill 2 acute leukaemia | Chicken | | Ser/ThrPK |

TABLE 4-continued

Oncogenes and tumor viruses

| Acronym | Virus | Species | Tumor origin | Comments |
|---|---|---|---|---|
| mos | Moloney sarcoma | Mouse | | Ser/ThrPK |
| myb | Myeloblastosis | Chicken | Leukaemia | Nuclear, TR |
| myc | MC29 myelocytomatosis | Chicken | Lymphomas | Nuclear TR |
| N-myc | NVT | Human | Neuroblastomas | Nuclear |
| neu (ErbB2) | NVT | Rat | Neuroblastoma | TryPK GFR L |
| ral (mil)[b] | 3611 sarcoma | Mouse | | Ser/ThrPK |
| Ha-ras | Harvey murine sarcoma | Rat | Bladder, mammary and skin carcinomas | GTP-binding |
| Ki-ras | Kirsten murine sarcoma | Rat | Lung, colon carcinomas | GTP-binding |
| N-ras | NVT | Human | Neuroblastomas leukaemias | GTP-binding |
| rel | Reticuloendothe-liosis | Turkey | | |
| ros | UR2 | Chicken | | TyrPK GFR L |
| sis | Simian sarcoma | Monkey | | One chain of PDGF |
| src | Rous sarcoma | Chicken | | TyrPK |
| ski | SKV770 | Chicken | | Nuclear |
| trk | NVT | Human | Colon carcinoma | TyrPK GFR L |
| yes | Y73, Esh sarcoma | Chicken | | TyrPK(src) |

In another embodiment, the anti-neoplastic agent used is a cellular matrix inhibitor. More preferably, the cellular matrix inhibitor is an anti-cellular-matrix antibody or an anti-cellular-matrix antisense oligonucleotide. For example, antibodies and antisense oligonucleotides against the following cellular matrix or cellular matrix gene can be used: caveolin-1, decorin, cadherins, catenins, integrins.

In a specific embodiment, the combination further comprises a tumor suppressor gene for combined intratumoral therapy and gene therapy. In a preferred embodiment, the tumor suppressor gene used is p16, p21, p27, p53, RB, WT-1, DCC, NF-1 and APC. In another specific embodiment, the combination further comprises a suicide gene such as HSV1tk (herpes simplex virus 1 thymidine kinase), tdk&tmk (thymidine kinase & thymidylate kinase), coda&upp (cytosine deaminase & uracil phophoribosyl transferase); a cytolytic gene such as granzyme A, Granzyme B, perforin; or an apoptotic gene such as Bak, Bax, Bcl-XL, Bcl-XS, Bik, Sarp-2, TRAIL. In still another specific embodiment, the combination further comprises a cytokine gene, such as IL-1β, IL-2, IL-4, IL-6, IL-8, IL-10, IL-12, IL-15, GM-CSF, IFN-α, IFN-β, IFN-γ, TNF-α, B7.1 or b7.2 to enhance the immune response.

The gene can be used in the form of naked DNA, complexed DNA, cDNA, plasmid DNA, RNA or other mixtures thereof as components of the gene delivery system. In another embodiment, the tumor suppressor gene is included in a viral vector. Any viral vectors that are suitable for gene therapy can used in the combination. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and Vaccinia virus vectors can be used. In addition, the genes can be delivered in a non-viral vector system such as a liposome wherein the lipid protects the DNA or other biomaterials from oxidation during the coagulation.

In another specific embodiment, the combination further comprises a radiation sensitizer for combined intratumoral therapy and radiation therapy. In a preferred embodiment, the radiation sensitizer used is SR 2508 (etanidazole) (Chang et al., *Int. J. Radiat. Oncol. Biol. Phys.*, 40(1):(65-70 (1998)) or Buthionine sulfoximine(BSO) (Vahrmeijer et al., *Cancer Chemother. Pharmacol.*, 44(2):111-6 (1999)).

In a specific embodiment, the combination further comprises a facilitating agent that facilitates conjugation between the hapten and a tumor antigen to enhance the autologous tumor-specific immune response. Preferably, the facilitating agent used is a chelator or a chemical linking agent. More preferably, the chelator used is glycyltyrosyl-(N-e-diethylenetriaminepetaacetic acid)-lysine (GYK-DTPA) (Abdel-Nabi and Doerr, *Targeted Diagn. Ther.*, 6:73-88 (1992)) or doxorubicin adipic-dihydrazide (ADR-ADH). Also more preferably, the chemical linking agent used is carbodiimide.

In another specific embodiment, the combination further comprises an immune response potentiator to enhance the autologous tumor-specific immune response. Preferably, the immune response potentiator used is Bacille Calmette-Guerin (BCG) (Ratliff, *Eur. Urol.*, 2:17-21 (1992)), Corynebacterium Parvum (Lillehoj et al., *Avian Dis.*, 37(3):731-40 (1993)), Brucella abortus extract, glucan, levamisole, tilorone, an enzyme, a non-virulent virus, polysaccharides, or herb extracts such as Chinese herb extracts. More preferably, the enzyme used is Vibrio cholera neuraminidase (VCN) (Seiler and Sedlacek, *Recent Results Cancer Res.*, 75:53-60 (1980)), Papain (Helting and Nau, *Acta Pathol. Microbiol. Immunol. Scand.*, 92(1):59-63 (1984); and Hess, *Eur. J. Immunol.*, 6(3):188-93 (1976)), β-Gal or ConA. Also more preferably, the non-virulent virus used is a non-virulent Newcastle virus (Meulemans et al., *Vet. Rec.*, 143(11):300-3 (1998); and Adams, *Poult. Sci.*, 49(1):229-33 (1970)). Further more preferably, the polysaccharides used are anti-tumor polysaccharide from the mycelium of liquid-cultured *Agaricus blazei mill* (preliminarily glucomannan with a main chain of β-1,2-linked D-mannopyranosyl residues and β-D-glucopyranosyl-3-O-beta-D-glucopyranosyl residues as a side chain (Mizuno et al., *Biochem. Mol. Biol. Int.*, 47(4):707-14 (1999)); anti-tumor polysaccharide preparation from *Flammulina velutipes* (The backbones of the polysaccharide is mainly composed of β-(1→3)-D-linked glucose and its molecular weight was estimated to be about 200 kD) (Leung et al., *Immunopharmacology*, 35(3):255-63 (1997)); sizofiran (SPG) (Tanji et al., *Yakugaku Zasshi*, 110(11):869-75 (1990)); schizophyllan (Sakagami et al., *Biochem. Biophys. Res. Commun.*, 155(2):650-5 (1988)); mannan (Gavrilenko et al., *Vopr. Onkol.*, 29(4):67-70 (1983)); lentinan (Haba et al., *Int. J, Cancer*, 18(1):93-104 (1976)); Su-polysaccharide (Su-Ps) (Kumazawa et al., *Gan To Kagaku Ryoho*, 14(12):3329-35 (1987)); or mannozym (Zastrow, *Padiatr. Grenzgeb.*, 24(3:229-36 (1985)).

In another specific embodiment, the combination can include a coagulation lysing agent to enhance the autologous tumor-specific immune response. Preferably, the coagulation lysing agent used is proteinase K, Glycosyl-phosphatidylinositol-B7 (Brunschwig et al., *J. Immunother.*, 22(5):390-400 (1999); and McHugh et al., *Cancer Res.*, 59(10):2433-7 (1999)) and pancreatin.

In yet another specific embodiment, the combination can include a cytokine to enhance the autologous tumor-specific immune response. Preferably, the cytokine is administered as a liposome-encapsulated IL-2 for depot formulation (Krup et al., *J. Immunother.*, 22(6):525-38 (1999)), or a GM-CSF depot formulation (Leong et al., J. Immunother., 22(2):166-74 (1999)).

In yet another specific embodiment, the combination further can include an oncogene to enhance the autologous tumor-specific immune response. Preferably, the oncogenes set forth in the above Table 4 can be used.

In another embodiment, the combination can include an attenuated, replication-competent virus vector to enhance the autologous tumor-specific immune response. Preferably, the attenuated, replication-competent virus vector used is the herpes simplex virus type 1 (HSV-1) mutant G207, which is able to replicate in human tumor cells with resultant cell death and tumor growth inhibition, yet is nonpathogenic in normal tissue (Toda et al., *Hum. Gene. Ther.*, 10(3):385-93 (1999)).

In another embodiment, the combination can include a reporter to monitor the treatment progress. The reporter can be a chemical or an enzyme. Preferably, the reporter enzyme is β-galactosidase or its gene. Other reporters known in the art are also contemplated.

In on exemplary embodiment, the combination includes $H_2O_2$ as the oxidizing agent, ethanol as the protein denaturing agent, TNP as the hapten. It may also include carbodiimide as a facilitating agent.

The oxidizing agent or reducing agent is administered in a composition at a concentration from about 0.01% (w/w) to about 35% (w/w), the protein denaturing agent is from about 1% (w/w) to about 98% (w/w) and the hapten is from about 1 mg/ml to about 80 mg/ml in the combination.

Also provided herein are kits for use in intratumoral therapy, which kit include the combination which includes compositions containing one or more of a) an oxidizing agent or a reducing agent; b) a protein denaturing agent; and c) a hapten. The kit can also include syringes for administering the composition(s) and instructions for administration.

Also provided herein is an article of manufacture for use in intratumoral therapy. The article of manufacture includes a) packaging material; b) a one or more of an oxidizing agent or a reducing agent, a protein denaturing agent, and a hapten; and c) a label indicating that the article is for treating neoplasms.

C. Methods of Treatment

Provided herein are methods for treating neoplasm in a mammal by in situ administration to a neoplasm of a mammal an effective amount of a hapten and coagulation agent(s) or treatment(s) that causes coagulation of the neoplasm, whereby an autologous immune response is generated against the neoplasm and the neoplasm is treated. In a specific embodiment, the mammal treated is a human.

In another specific embodiment, the hapten used is trinitrophenol (TNP), dinitrophenol (DNP), N-iodoacetyl-N'-(5-sulfonic 1-naphtyl) ethylene diamine (AED), dinitrofluorobenzene(DNFB) and Ovabulin (OVA).

In still another specific embodiment, the method further comprises in situ administering a facilitating agent that facilitates conjugation between the hapten and a tumor antigen of the neoplasm to enhance the tumor-specific autologous immune response. Preferably, the facilitating agent used is a chelator or a chemical linking agent. More preferably, the chelator used is glycyltyrosyl-(N-e-diethylenetriaminepetaacetic acid)-lysine (GYK-DTPA) or doxorubicin adipic-dihydrazide (ADR-ADH). Also more preferably, the chemical linking agent is carbodiimide.

In yet another specific embodiment, the method further comprises in situ administering an immune response potentiator to enhance the tumor-specific autologous immune response. Preferably, the immune response potentiator used is Bacille Calmette-Guerin (BCG) (Ratliff, *Eur. Urol*, 2:17-21 (1992)), Corynebacterium Parvum (Lillehoj et al., *Avian Dis.*, 37(3):731-40 (1993)), Brucella abortus extract, glucan, levamisole, tilorone, an enzyme, a non-virulent virus, polysaccharides, or herb extracts such as Chinese herb extracts. More preferably, the enzyme used is Vibrio cholera neuraminidase (VCN), Papain, β-Gal or ConA. Also more preferably, the non-virulent virus used is a non-virulent Newcastle virus.

In yet another specific embodiment, the method further comprises in situ administering a coagulation lysing agent to enhance the tumor-specific autologous immune response. Preferably, the coagulation lysing agent used is proteinase K, Glycosyl-phosphatidylinositol-B7 or pancreatin.

Any means that can coagulate neoplasm tissues or cells, e.g., chemical or physical means, can be used. In a specific embodiment, coagulation of neoplasms is achieved by in situ administration of a combination comprising: a) an oxidizing agent or a reducing agent; and b) a protein denaturing agent.

The oxidizing or reducing agent, the protein denaturing agent and the hapten can be formulated in a single pharmaceutical composition or each can be formulated in a separate pharmaceutical composition.

In a specific embodiment, the oxidizing agent used is hydrogen peroxide ($H_2O_2$), ozone, polyatomic oxygen $O_7$, polyatomic oxygen $O_8$, $NaIO_4$, potassium peroxymonosulfate (oxone) (Wozniak et al., *Bioorg. Med. Chem. Lett.*, 8(19):2641-6 (1998)), D,L-S-methyllipoic acid methyl ester (Pan and Jordan, *Biochemistry*, 37(5):1357-64 (1998)), tertiary butyl hydroperoxide (Tarin et al., *Mol. Hum. Reprod.*, 2(12):895-901 (1996)), menadione (Santini et al., *Free Radic. Biol. Med.*, 20(7):915-24 (1996)), diamide (Bosin and Kasper, *J. Biochem. Toxicol.*, 7(3):139-45 (1992)), iodogen (Saha et al., *Int. J. Rad. Appl. Instrum.*, 16(4):431-3 (1989)), N-bromosuccinimide (Sinn et al., *Anal. Biochem.*, 170(1):186-92 (1988)), omeprazole (Irn et al., *J. Biol. Chem.*, 260(8):4591-7 (1985)), or N-ethylmaleimide (Marzulli et al., *Boll. Soc. Ital. Biol. Sper.*, 61(1):121-7 (1985)).

In another specific embodiment, the reducing agent used is hematoxylin, a hypoxic reducing agent such as a nitroimidazole, or nonnitro compound SR 4233.

In still another specific embodiment, the protein denaturing agent used is an alcohol, guanidine hydrochloride, guanidinium thiocyanate, sodium citrate, 2-mercaptoethanol, sarcosyl, phenol, chloroform or urea. For example, methyl, ethyl, n-propyl, n-butyl, n-pentyl, n-hexyl, n-heptyl, n-octyl, n-decyl, n-dodecyl, n-tetradecyl, n-hexadecyl, n-octadecyl, isopropyl, isobutyl, sec-butyl, tert-butyl, isopentyl, activeamyl, tert-pentyl, cyclopentanol, cyclohexanol, allyl, crotyl, methylvinylmethanol, benzyl, a-phenylethyl, β-phenylethyl, diphenylmethanol, triphenylmethanol, cinnamyl, 1,2-ethanediol, 1,2-propanediol, 1,3-propanediol, glycerol or pentaerythritol alcohol can be used in the treatment. Preferably, the alcohol used is ethanol. Protein denaturation can also be achieved by chemical or physical treatment to reach acidic condition, e.g., pH from about 2 to about 5.

The presently contemplated intratumoral therapy can be used alone or can be used in conjunction with other cancer therapies. In a specific embodiment, the intratumoral therapy is used in conjunction with chemotherapy by further comprising in situ administering an anti-neoplasm agent to the neoplasm.

Any anti-neoplasm agents can be used. In a preferred embodiment, the anti-neoplasm agent is an anti-angiogenic agent. More preferably, the anti-angiogenic agent used is an inhibitor of basement membrane degradation, an inhibitor of cell migration, an inhibitor of endothelial cell proliferation, an inhibitor of three-dimensional organization and establishment of potency. Also more preferably, the anti-angiogenic agent used is AGM-1470 (TNP-470), angiostatic steroids, angiostatin, antibodies against avβ3, antibodies against bFGF, antibodies against IL-1, antibodies against TNF-α, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, gelatinase inhibitor, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, matrix metalloproteinase inhibitor, marimastat (BB-2516), medroxyprogesterone, 6-methylmercaptopurine riboside, metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4 (PF4), prednisolone, prolactin (16-Kda fragment), proliferin-related protein, prostaglandin synthase inhibitor, protamine, retinoids, Roquinimex (LS-2616. linomide), somatostatin, stromelysin inhibitor, substance P, suramin, SU101, tecogalan sodium (DS-4152), tetrahydrocortisol-sthrombospondins (TSPs), tissue inhibitor of metalloproteinases (TIMP 1, 2, 3), vascular endothelial growth factor inhibitors, vitamin A, Vitaxin, vitreous fluids, thalidomide, 3-aminothalidomide, 3-hydroxythalidomide and metabolites or hydrolysis products of thalidomide, 3-aminothalidomide, or 3-hydroxythalidomide. Other anti-angiogenic agents described in Section B can also be used. Also preferably, the anti-angiogenic agent used is an angiostatic gene such as angiostain, endostain, kringle-5, PEX, TIMP-1, TIMP-2, TIMP-3, TIMP-4, endo::angio, or endo::PEX; or an angiostatic chemokine genes such as IP-10, Mig, or SDF-1α.

In another preferred embodiment, the anti-neoplasm agent used is an alkylating agent, an antimetabolite, a natural product, a platinum coordination complex, an anthracenedione, a substituted urea, a methylhydrazine derivative, an adrenocortical suppressant, a hormone, an antagonist, an anti-cancer polysaccharide, or herb extracts such Chinese herb extracts. Additional anti-neoplasm agents described in Section B can also be used.

In still another preferred embodiment, the anti-neoplasm agent used is an oncogene inhibitor such as an anti-oncogene antibody or an anti-oncogene antisense oligonucleotide. For example, anti-oncogene antibodies or anti-oncogene antisense oligonucleotides against the following oncogenes can be used: abl, erbA, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

In another specific embodiment, the intratumoral therapy is used in conjunction with gene therapy by further comprising in situ administering a tumor suppressor gene sequence to the neoplasm. Preferably, the tumor suppressor gene sequence used isp16, p21, p27, p53, RB, WT-1, DCC, NF-1 and APC. In another specific embodiment, the method further comprises in situ administering a suicide gene such as HSVItk (herpes simplex virus 1 thymidine kinase), tdk&tmk (thymidine kinase & thymidylate kinase), coda&upp (cytosine deaminase & uracil phophoribosyl transferase); a cytolytic gene such as granzyme A, Granzyme B, perforin; or an apoptotic gene such as Bak, Bax, Bcl-XL, Bcl-XS, Bik, Sarp-2, TRAIL. In still another specific embodiment, the method further comprises in situ administering a cytokine gene, such as IL-1β, IL-2, IL-4, IL-6, IL-8, IL-10, IL-12, IL-15, GM-CSF, IFN-α, IFN-β, IFN-γ, TNF-α, B7.1 or b7.2 to enhance the immune response.

The gene can be used in the form of naked DNA, complexed DNA, cDNA, plasmid DNA for the combination components of gene delivery system. In another preferred embodiment, the tumor suppressor gene sequence is carried in a viral vector. Any viral vectors that are suitable for gene therapy can used in the combination. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vector expressing interested genes and Vaccinia virus vector can be used. In addition, the genes can be delivered in a non-viral vector system such as a liposome wherein the lipid protects the DNA or other biomaterials from oxidation during the coagulation.

In another specific embodiment, the method further comprises in situ administering a radiation sensitizer for combined intratumoral therapy and radiation therapy. In a preferred embodiment, the radiation sensitizer used is antisense raf oligodeoxyribonucleotide (Gokhale et al., *Antisense Nucleic Acid Drug Dev.*, 9(2):191-201 (1999); SR 2508 (etanidazole) (Chang et al., *Int. J. Radiat. Oncol. Biol. Phys.*, 40(1):65-70 (1998)) or Buthionine sulfoximine(BSO) (Vahrmeijer et al., *Cancer Chemother. Pharmacol.*, 44(2):111-6 (1999)).

In yet another specific embodiment, the method further comprises in situ administering a cytokine-containing depot to enhance the autologous tumor-specific immune response. Preferably, the cytokine-containing depot used is a liposome-encapsulated IL-2 as a depot formulation (Krup et al., *J. Immunother.*, 22(6 :525-38 (1999)), or a GM-CSF depot formulation (Leong et al., *J. Immunother.*, 22(2):166-74 (1999)).

In yet another specific embodiment, the method further comprises in situ administering an oncogene sequence to enhance the autologous tumor-specific immune response. Preferably, the oncogene sequences disclosed in the above Table 4 can be used.

In yet another specific embodiment, the method further comprises in situ administering an attenuated, replication-competent virus vector to enhance the autologous tumor-specific immune response. Preferably, the attenuated, replication-competent virus vector used is the herpes simplex virus type 1 (HSV-1) mutant G207, which is able to replicate in human tumor cells with resultant cell death and tumor growth inhibition, yet is nonpathogenic in normal tissue (Toda et al., *Hum. Gene. Ther.*, 10(3):385-93 (1999)).

In yet another specific embodiment, the method further comprises in situ administering a reporter to monitor the treatment progress. The reporter can be a chemical or an enzyme. Preferably, the reporter enzyme is β-galactosidase or its gene. Other reporters known in the art are also contemplated.

In a specific embodiment, $H_2O_2$ as the oxidizing agent, ethanol as the protein denaturing agent and TNP as the hapten are used in the treatment.

In another specific embodiment, the oxidizing agent or reducing agent used is from about 0.01% (w/w) to about 35% (w/w), the protein denaturing agent used is from about 1% (w/w) to about 99% (w/w) and the hapten used is from about 1 mg/ml to about 80 mg/ml in the treatment.

Coagulation of neoplasm tissues or cells can also be achieved by physical treatment, e.g., cryotherapy (Morris, *HPB Surg.*, 9(2):118-20 (1996); Seifert et al., *World J. Surg.*, 23(10):1019-26 (1999); and August, *Clin. Dermatol.*, 13(6): 589-92 (1995)), laser coagulation (ILC) (Jocham, *Recent Results Cancer Res.*, 126:135-42 (1993); Chang et al., *Br. J. Plast. Surg.*, 52(3):178-81 (1999); and Jiao and Habib, *Br. J. Surg.*, 86(9):1224 (1999)), percutaneous microwave coagulation therapy (Ohmoto et al., *Am. J. Roentgenol.*, 173(5): 1231-3 (1999); Seki et al., *Am. J. Gastroenterol.*, 94(2):322-7 (1999); and Shibata et al., *Gan To Kagaku Ryoho*, 26(12): 1760-3 (1999)), radio-frequency-induced coagulation necrosis (Francica and Marone, *Eur. J. Ultrasound.*, 9(2):145-53 (1999); Goldberg et al., *Radiology*, 209(2):371-9 (1998); Goldberg et al., *Radiology*, 213(2):438-44 (1999); and Goldberg et al., *Radiology*, 209(3):761-7 (1998)), transpupillary thermotherapy (Shields et al., *Ophthalmology*, 105(4):581-90 (1998); Strmen and Furdova, *Cesk. Slov. Oftalmol.*, 55(3): 176-80 (1999), ultrasonictherapy (Lu et al., *Int. J. Hyperthermia*, 12(3):375-99 (1996); and Saitoh et al., *Urology*, 43(3): 342-8 (1994)) or radiationtherapy (Popov, *Med. Radiol. (Mosk)*, 28(6):55-8 (1983); and Strashinin et al., *Vopr. Onkol.*, 17(1):78-9 (1971)).

In a specific embodiment, the autologous immune response generated by the combined action of the hapten and the coagulation agent or treatment is a humoral and/or cellular immune response.

Any neoplasm, tumor or cancer can be treated by the presently contemplated methods. For example, the neoplasm of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve or vulva neoplasm can be treated.

Other examples of tumors or cancers treatable by the present methods include breast cancer, lung cancer, colonrectal cancer, tumor of the pancreas, gallbladder and extrahepatic ducts, tumor of liver, gastric neoplasms, cancer of the esophagus, malignant melanoma, urologic and male genitals cancers, skin cancer, head neck and thyroid cancer, cancer of the central nervous system and pituitary, tumor of the eye and ocular adnexa, malignant tumor of bone, soft tissue sarcoma, Hodgkin's disease and non-Hodgkin's disease, multiple myeloma, pediatric solid tumor, gynecologic cancer. Additional examples include:

A. Tumor of mesenchymal origin:
  (1) Connective tissue and derivatives: Sarcomas: fibrosarcoma, myxosarcoma, liposarcoma, chondrosarcoma, osteogenic sarcoma
  (2) Endothelial and related tissues blood vessels: angiosarcoma, lymphangiosarcoma, synovioma, mesotheliomas, invasive meningioma B. Tumor of epithelial origin:
  (1) Stratified squamous: carcinoma, squamous cell or epidermoid carcinoma
  (2) Basal cells of skin or adnexa: basal cell carcinoma
  (3) Skin adnexalglands: Sweat gland carcinoma, sebaceous gland carcinoma
  (4) Epithelial lining: Adenocarcinoma, papillary carcinoma, papillary adenocarcinoma, cystadenocarcinoma, medullary carcinoma, undifferentiated carcinoma
  (5) Respiratory passage: Bronchogenic adenoma
  (6) Neuroectoderm: Melanoma,
  (7) Renal epithelium: Renal cell carcinoma, hypemephroma
  (8) Liver cells: Hepatoma (hepatocellular carcinoma)
  (9) Bile duct: Bile duct carcinoma, chlangiocarcinoma
  (10) Urinary tract epithelium: Papillary carcinoma, transitional cell carcinoma, squamous cell carcinoma
  (11) Placental epithelium: Choriocarcinoma
  (12) Testicular epithelium (germ cells): Seminoma, embryonal carcinoma.

Further, tumors derived from more than one neoplastic cells types or derived from more than one germ layers are also treatable.

In a preferred embodiment, the neoplasm to be treated is a solid tumor. More preferably, the size of the solid tumor is larger than $10^8$ cells. Most preferably, the size of the solid tumor is from about $5 \times 10^9$ to about $10^{11}$ cells.

In another preferred embodiment, the hapten and the coagulation agent(s) are administered to the neoplasm via injection. For better distribution of the injected solution in tumor, the solution can be injected slowly with high pressure, e.g., up to 6 AMP, injector or syringe. The solution can also be injected with a 15-35 gauge needle. During the injection, the tip of needle can be turned around in tumor by turning the handle of the needle. Injection doses and frequency should be adjusted according to the nature, size and location of the tumor, and the progress of the treatment. Injection channels can be prepared for better distribution of the solution in tumor prior to the actual injection using spinal needle for preinjection into the tumor before the injection of solution. Injection can also be performed under the guidance of CT, MR, ultrasound and other suitable imaging technologies.

In a specific embodiment, methods and device disclosed in U.S. Pat. No. 5,651,986 can be used for controlled local delivery of the hapten and coagulation agents to solid tumor. U.S. Pat. No. 5,651,986 discloses methods and devices for localized delivery of a chemotherapeutic agent to solid tumors, wherein the agent does not cross the blood-brain barrier and is characterized by poor bioavailability and/or short half-lives in vivo. The devices have reservoirs that release drug over an extended time period while at the same time preserving the bioactivity and bioavailability of the agent.

In still another preferred embodiment, the hapten and the coagulation agent(s) or treatment(s) are administered to the neoplasm in combination with a surgical procedure. For example, the administration of the hapten and the coagulation agent(s) or treatment(s) can be performed before, during or after a surgical procedure.

D. EXAMPLES

Example 1

Treatment with Chemotherapy

Thirty one advanced stage IV liver cancer patients were treated using the presently contemplated in-situ vaccination therapy. There are 24 male and 7 female patients in this group with an age range from 30 to 70 years old. Twenty patients have primary liver cancer: eighteen of these twenty patients have abnormal liver function; fourteen of these twenty patients have ascites; and all twenty cases have recent weight loss. The remaining eleven of the cancer patients have secondary liver cancer: five patients have liver metastasis cancer from the esophagus, two have liver metastasis cancer from the stomach, three have liver metastasis cancer from the colon and one has liver metastasis cancer from the lungs. Prior to the procedure, patients were given a mild sedative or painkiller. Patients were calmed thoroughly and were also monitored by modern medical imaging. With local anesthesia, percutaneous puncture was administered directly into the tumor using a spinal needle. The needle was connected to a high-power syringe containing a combination of ethanol, $H_2O_2$, anticancer drug AraC (8 mg/ml) and hemotoxilin (5 mg/ml). The combination was injected directly into the tumor and distributed throughout the matrix of the whole tumor. After administration, sonic-imaging showed the stranger echo imaging which indicated the coagulation area. Following the coagulation lysis and tumor cell death monitored by sonic-imaging, which showed liquefied echo, tumor started to shrink and disappear. The normal tissues grew replacing the tumor. This process was monitored by medical imaging systems. The amount of the ingredients of the combination injected into the tumor was determined by the diameter of tumors (in centimeters) with 2 ml of the combination for each centimeter. This procedure was repeated in one to two weeks. On average, each patient was treated with the injection for 3 times. Computer imaging database was established for further research to monitor the entire treatment procedure.

There were no severe side effects for all the treated patients. After one or two days, some patients experienced tolerable pain at the injection site. A few patients had a light fever during the first week. All side effects disappeared in about one week. No serious complications happened in any cases.

Therapeutic efficiency are summarized below:
1. Sonic-imaging picture shows that the treated tumor has enhanced echo imaging just one or two days after the treatment. One week after the treatment, the images of the sonic-imaging changed from enhanced echo imaging to a diminished echo imaging as a result of the coagulation and tumor cells lysis. Two weeks later, the sonic-imaging shows the central part of the tumor wherein the coagulation diminished echo imaging and only the outer margin of the tumor had enhanced echo, which means that the central part of the tumor has necrosis and was liquated by the coagulation. The enhanced echo imaging of the outer membrane of the tumor or coagulation is a natural inflammatory defense to fight the tumor live cells not initially killed by the coagulation. The membrane structure holds the necrosis tissue and anticancer drug within the tumor to further kill the remaining tumor cells. Following this stage, the continuing shrinkage of the tumor was observed.
2. Twenty seven (27) of the thirty one patients showed the shrinkage of the tumor, the four of the twenty one patients showed that the tumor vanished. Overall therapeutic efficacy is 100% while patients were still hospitalized.
3. Fifty percent of the ten patients with abnormal liver function showed the return of normal liver function.
4. In sixty four percent of the fourteen patients with ascites, ascites were reduced, and two patients completed recovered from ascites.

This study shows that the use of contemplated treatment generated local immune response to the tumor and anticancer drug eliminated the tumor in the patients body. Average survival time of this group is a year and a half.

Example 2

Treatment with Radiotherapy

Twenty esophagus carcinoma patients were treated with the contemplated methods with radiotherapy. The esophagus X-ray film showed that ten patients had middle of esophagus 3 to 4 cm tumor, another ten had 5 to 8 cm tumor burden. The clinical diagnosis was middle esophagus carcinoma. One patient was at IIa stage, T2N0M0, PKS score was 80. Another patient was at IIa, T3N0M0, with a cellular pathology diagnosis of squamocellular carcinoma. These patients were treated under esophagus endoscope direction. Needle was injected into tumor and the composition containing ethanol, $H_2O_2$, hapten and anticancer drug AraC was injected followed with radiation therapy in a dose of 60 Gy/30 times/6 weeks. Esophagus X-ray showed that the tumor disappeared. For one year and five months after the treatment, the patients have been in good condition and no local tumor recovery has been observed.

Sixteen patients with late stages of lung carcinoma were treated with the procedures described in paragraph 0191. One of these patients had surgery before the treatment; three had metastasis carcinoma; six patients had tumor in the central lung; and ten patients had tumor are at the side of lung. All patients had pathological diagnosis: squamocellular carcinoma in 9 cases and adenocarcinoma in 7 cases. There are 12 male patients and 4 female patients in this group with an age ranging from 35 to 85 years old. KPS score was from 40 to 80 with an average of 65.6. Five was in the IIa 5 stage, 4 was in the IIb stage and 7 was in the IV stage. All patients were subjected to the intratumoral injection of a composition containing Alcohol, $H_2O_2$, hapten, anticancer drug AraC and radiosensitizer SR 2508 under X ray simulator monitoring. The injection was followed with radiation therapy in the dose of 60 Gy/30 times/6 weeks. Therapeutic efficacy is the following: 93.8% in general; CR in 4 cases (25%); PR in 11 cases (68.8%); and SD in 1 case (6.3). KPS score increased for more than 10 degrees in each patient. All patients are still live for more than one year after the treatment.

Example 3

Treatment of Ovarian Carcinoma

One 56 year old female ovarian carcinoma patient had a surgery 8 years ago. The patient had a big mass in the lower abdomen before the treatment. Sonic-imaging showed a 5×4.1×3 cm size. The patient received chemotherapy that resulted in tumor growth. The patient was treated with composition containing ethanol, $H_2O_2$, anticancer drug AraC and hapten. Two weeks later, tumor size reduced to 3.4×3.5×2 cm. The patient have been feeling better and has normal blood cell counts.

Example 4

Treatment for Breast Cancer with Surgery

First patient, female, 34 year old, had pathological diagnosis of intraductal invasive carcinoma at right side breast. Two years ago, breast carcinoma was removed by surgery. Prior to the treatment with the presently provided methods, tumor metastasis occurred at ipsilateral supraclavicular lymph nodes. Sonic-imaging showed 1.31×0.97 cm and 7×6 cm size hard masses. Patient was treated with presently provided method with combination containing ethanol, $H_2O_2$, hapten, anticancer drug AraC. Tumor masses shrank to 0.3×0.6cm and 1.5×1.5 cm and appeasers as scars. The patient is in very good condition with normal blood cell counts.

Second patient, female, had a 3×3 cm mass in her left breast without lymph node metastasis. Pathological diagnosis is intraductal invasive carcinoma. She was treated with the methods as described for the first patient. After the treatment, tumor shrank to 1.1×1.9 cm scar in two weeks. Four months later, this scar was surgically removed. So far, tumor cells have not detected in the scar by pathological examination and the patient is in very good condition with normal blood cell counts.

Third patient, female and 54 years old, had a mass of 6×8×6 cm size in her left breast. Biopsy pathological diagnosis is adenocarcinoma, in clinical stage of T3N1Mo with one ipsilateral axillary lymph node metastasis. She was treated with the methods as described for the first patient for three weeks. One month later, tumor shrank a little bit. Two months after the treatment, the tumor was surgically removed and no tumor cells have been detected by pathological examination. The patient is in very good condition with normal blood cell counts.

Example 5

Treatment for Pancreatic Cancer

One patient, female, 68 years old, had pancreatic tumor with invasion of aorta vein. KPS score was 70 and sonic-imaging showed tumor size of 4.6×5.3 cm with an irregular ball shape. Clinical diagnosis was pancreas carcinoma in II stage, T3N1Mo. She was treated once with a combination containing ethanol, $H_2O_2$, hapten, anticancer drug AraC. In four weeks, tumor shrank to 3.7×4.5 cm. The patient is in very good condition with normal blood cell counts.

Example 6

Treatment of Colon Cancer

One patient, male, 68 years old, had colon cancer as shown by X-ray. Pathological diagnosis was carcinoid, sigmoidoscope with an 1.5×2 cm tumor at burden of colon and rectal, invasive to inside of colon and blocking the stool moving. Under the sigmoidoscope, tumor was injected twice in four days using the combination containing ethanol, $H_2O_2$, hapten, and anticancer drug AraC. Two days later, patient felt better with stool moving out. In three weeks, tumor disappeared. The patient is in very good condition with normal blood cell counts.

Example 7

Treatment with Immunological Adjuvant of Liver Cancer

One liver cancer patient, male, 56 year old, had Hepatitis B for 14 year. Sonic-imaging showed a mass in the right leaf of liver, size 5.7×4 cm, with a small size mass. KPS score was 60 and blood cell counts were: HB14g/l, wbc4.5×10/L, L0.38/1, M:0.04/L, and AFP>400 ug/L. Clinical diagnosis was primary liver cancer in stage II and T2N0M0. Pretreatment was low-dose (200 to 300 mg/m$^2$) cycclosphamide IV drop for three days. The bigger tumor was injected twice in two weeks with a combination containing ethanol, $H_2O_2$, hapten, anticancer drug AraC and BCG. The treatment was followed by GM-CSF injection for 3 weeks. After the first treatment was performed, the patient felt a little pain at the injection site and had a fever not exceeding 38° degree for two days. In three weeks, the big liver tumor shrank to 4×4 cm and small tumor shrank too. The patient has been in very good condition now for six months with a KPS score 80 and normal blood cell counts.

One liver cancer patient, male and 71 years old, had left live mass as found by CT scanning with a size of 3.3×3.6 cm. KPS score was 70 and blood counts were the following: hb14.8/L, wbc:4.3×10/L, L:0.38, M:0.02, and AFP>400 ug/L. Sonic imaging showed a 4.7×5.7 cm tumor mass. Clinical diagnosis was primary liver cancer in stage II and T2NoMo. Pretreatment was low-dose (200 to 300 mg/m$^2$) cyclosphamide IV drop for three days. Tumor was injected with a combination containing ethanol, $H_2O_2$, hapten, anticancer drug AraC and BCG. The treatment was followed by GM-CSF injection for 3 weeks. Patient felt a little pain at the local injection site and had a fever not exceeding 38° degree for five days. Tumor shrank to 3×4 cm two weeks later. Another injection was performed for further therapeutic efficacy. The patient has been in very good condition with the blood counts of HB12g/L, WBC:8.84×10/L, L:0.20, and M:0.02.

One patient, male, 74 years old, had primary tumor from kidney carcinoma. Two years ago, the kidney carcinoma was surgically removed. CT and sonic-imaging showed multiple-masses in the liver, about 26 masses in the whole liver. The patient weighed 95 kg with KPS of 60 and blood counts as the following: HB12 g/L, and wbc 8.5×10/L. Liver functioned normally. Pretreatment was low-dose (200 to 300 mg/m$^2$) cyclosphamide IV drop for three days. The injection were performed 5 times for 12 tumor masses using a combination containing ethanol, $H_2O_2$, hapten, anticancer drug AraC and BCG. The treatment was followed by GM-CSF injection for 3 weeks. Patient felt a little pain at the local injection site. Sonic-imaging showed that the 12 tumor masses in the liver shrank in different degrees. The two bigger masses disappeared and the non injected tumor masses also shrank while some tumors did not change very much in size. The patient has been in very good condition with normal blood cell counts and normal liver function. This study shows that the use of the presently provided composition with immunological adjuvant is advantageous to other therapy in that treatment of one target tumor can result in the shrink of another tumor.

Example 8

Additional Examples of Treatment of Liver, Lung and Esophageal Cancer Patients

TABLE 5

Responses to Treatment for Primary Liver Cancers

| Stages | CR | PR | NC | PD | Totals |
|---|---|---|---|---|---|
| I | | | | | |
| II | | | 1 | | 1 |
| III | | 6 | 17 | 1 | 24 |
| IV | | 10 | 35 | 1 | 46 |
| Totals | | 16 | 53 | 2 | 71 |
| Response Rate | | 22.5% | 74.6% | 2.8% | |

CR: complete response;
PR: partial response;
NC: no change;
PD: cancer progress

For patients having un-resectable adult primary liver cancer, known treatment, e.g., treatment using chemotherapeutic agents infused with a subcutaneous portal or implantable pump via catheter has demonstrated response in 15% to 30% of the patients, but no significant survival benefits have been conclusively demonstrated. For patients having stages III to IV liver cancer, median survival time using known treatment is usually 2 to 4 months. In contrast, when patients having un-resectable adult primary liver cancer were treated with the methods described in Example 1, i.e., using a combination of ethanol, $H_2O_2$, anticancer drug AraC and hemotoxilin, the sum of total and partial response rate is more than 95% (see Table 5).

TABLE 6

Calculation of Cumulative Survival Rates for the Imaging Clinical Trial Data

| Time (months) | No. at risk | No. of deaths | Surviving this time | Cumulative Survival. |
|---|---|---|---|---|
| 1 | 34 | 3 | 31 | 31/34 = 91.8% |
| 2 | 31 | 6 | 25 | 0.91 × 25/31 = 73% |
| 3 | 25 | 1 | 24 | 0.73 × 24/25 = 70% |
| 4 | 24 | 4 | 20 | 0.70 × 20/24 = 58.8% |
| 5 | 20 | 3 | 17 | 0.58 × 17/20 = 50% |
| 6 | 17 | 2 | 15 | 0.50 × 15/17 = 44.12% |
| 7 | 15 | 0 | 15 | 44.12% |
| 8 | 15 | 1 | 14 | 41.18% |
| 9 | 14 | 0 | 14 | 41.18% |
| 10 | 14 | 3 | 11 | 32.35% |
| 11 | 11 | 0 | 11 | 32.35% |
| 12 | 11 | 0 | 11 | 32.35% |
| 13 | 11 | 1 | 10 | 29.41% |
| 14 | 10 | 0 | 10 | 29.41% |
| 15 | 10 | 2 | 8 | 23.53% |
| 16 | 8 | 0 | 8 | 23.53% |
| 17 | 8 | 1 | 7 | 20.59% |

For stages III or IV liver cancer, patients usually die in 4 to 6 months with known treatment. The average of 5-year survival rate for these patients is about 5%. In contrast, the one year survival rate of the patient treated with the methods described in Example 1, i.e., using a combination of ethanol, $H_2O_2$, anticancer drug AraC and hemotoxilin, is close to 30% (see Table 6).

TABLE 7

Responses to Treatment for Secondary Liver cancers

| Stages | CR | PR | NC | PD | Totals |
|---|---|---|---|---|---|
| I | | | | | |
| II | | | | | |
| III | | | | | |
| IV | 2 | 18 | 19 | 2 | 41 |
| Totals | 2 | 18 | 19 | 2 | 41 |
| Response Rate | 4.9% | 44% | 46.3% | 4.9% | |

TABLE 8

Calculation of Cumulative Survival Rates for Secondary liver Cancer Trial

| Time (months) | No at risk | No of deaths | Surviving this time | Cumulative Survival. |
|---|---|---|---|---|
| 1 | 16 | 2 | 14 | 14/16 = 87.5% |
| 2 | 14 | 0 | 14 | 87.5% |
| 3 | 14 | 2 | 12 | 75% |
| 4 | 12 | 3 | 9 | 56.25% |
| 5 | 9 | 0 | 9 | 56.25% |
| 6 | 9 | 0 | 9 | 56.25% |
| 7 | 9 | 1 | 8 | 50% |
| 8 | 8 | 0 | 8 | 50% |
| 9 | 8 | 1 | 7 | 43.75% |
| 10 | 8 | 1 | 7 | 43.75% |
| 11 | 8 | 1 | 7 | 43.75% |
| 12 | 8 | 1 | 7 | 43.75% |
| 13 | 7 | 1 | 6 | 37.5% |

TABLE 9

Responses to Treatment of Non-Small Cell Lung Cancers

| Stages | CR | PR | NC | PD | Totals |
|---|---|---|---|---|---|
| IIb | | 1 | 1 | | 2 |
| IIIa | | | 1 | | 1 |
| IIIb | | 4 | 5 | | 9 |
| IV | | | 8 | | 8 |
| Totals | | 5 | 15 | | 20 |
| Response Rate | | 25% | 75% | | |

TABLE 10

Responses to Treatment of NSCLC with Radiation Therapy

| Stages | CR | PR | NC | PD | Totals |
|---|---|---|---|---|---|
| Ia | 1 | | | | 1 |
| Ib | | 1 | | | 1 |
| IIa | | | | | |
| IIb | | 2 | | | 2 |
| IIIa | 1 | 9 | 4 | | 14 |
| IIIb | 2 | 8 | 1 | | 11 |
| IV | 2 | 5 | 5 | | 12 |
| Totals | 6 | 25 | 10 | | 41 |
| Response Rate | 14.6% | 61% | 24.3% | | |

CR + PR = 75.6%.

For patients having stage IIIa non-small cell lung cancers, no complete response to radiation therapy has been reported. In contrast, complete response in some patients treated with the combination of ethanol, $H_2O_2$, anticancer drug AraC and hemotoxilin coupled with radiation therapy (see example 2)

has been observed (see Table 10). For patients having stages IIIb and IV non-small cell lung cancers, response rate to single-agent therapy is in the range of 21% to 24% with known methods. Even with paclitaxel plus carboplatin double regimen, response rates have been in the range of 27% to 53%. In contrast, the response rate of comparable patients using the treatment methods described in Example 2 is about 75.6% (see Table 10).

TABLE 11

Calculation of Cumulative Survival Rates for NSCLC Clinical Trial Data

| Time (months) | No at risk | No of deaths | Surviving this time | Cumulative Survival. |
|---|---|---|---|---|
| 1 | 31 | 2 | 29 | 29/31 = 93.5% |
| 2 | 29 | 1 | 28 | 0.935 × 28/29 = 90.3% |
| 3 | 28 | 2 | 26 | 83.87% |
| 4 | 26 | 1 | 25 | 80.65% |
| 5 | 25 | 2 | 23 | 74.19% |
| 6 | 23 | 0 | 23 | 74.19% |
| 7 | 23 | 1 | 22 | 70.97% |
| 8 | 22 | 2 | 20 | 64.52% |
| 9 | 20 | 2 | 18 | 58.06% |
| 10 | 18 | 0 | 18 | 58.06% |
| 11 | 18 | 0 | 18 | 58.06% |
| 12 | 18 | 2 | 16 | 51.61% |
| 13 | 16 | 0 | 16 | 51.61% |
| 14 | 16 | 0 | 16 | 51.61% |
| 15 | 16 | 1 | 15 | 48.31% |
| 16 | 15 | 0 | 15 | 48.31% |
| 17 | 15 | 0 | 15 | 48.31% |
| 18 | 15 | 0 | 15 | 48.31% |
| 19 | 15 | 0 | 15 | 48.31% |
| 20 | 14 | 1 | 13 | 41.94% |

For patients having stage IIIa non-small cell lung cancers, without or without a successful chemotherapy, the average survival time is about 6 months, and only 10% of these patients will be alive at the end of one year. With conventional chemotherapy, the response rate is about 25% to 30% with the average survival time being about 8 or 9 months. With improved conventional chemotherapy, the one year survival rate can be improved to about 25%, and a recognizable, although small, proportion of patients (approximately 5%) can survive for 2 years. The present methods as described in Examples 1 and 2 improve the one year survival rate to 51.61% and one and half year survival rate to 42% (see Table 11).

TABLE 12

Responses to Treatment for Esophageal Cancers

| Stages | CR | PR | NC | PD | Totals |
|---|---|---|---|---|---|
| I | | | | | |
| II | 9 | 4 | 1 | | 14 |
| III | 9 | 7 | | | 16 |
| IV | 4 | 6 | 15 | 1 | 26 |
| Totals | 22 | 17 | 16 | 1 | 56 |
| Response Rate | 39.8% | 30% | 28.5% | 1.78% | |

TABLE 13

Calculation of Cumulative Survival Rates for Esophageal Cancer Trial

| Time (months) | No at risk | No of deaths | Surviving this time | Cumulative Survival |
|---|---|---|---|---|
| 1 | 15 | 3 | 12 | 12/15 = 80% |
| 2 | 12 | 0 | 12 | 80% |
| 3 | 12 | 0 | 12 | 80% |
| 4 | 12 | 0 | 12 | 80% |
| 5 | 12 | 1 | 11 | 73.35% |
| 6 | 11 | 0 | 11 | 73.35% |
| 7 | 11 | 0 | 11 | 73.35% |
| 8 | 11 | 0 | 11 | 73.35% |
| 9 | 11 | 1 | 10 | 66.67% |
| 10 | 10 | 0 | 10 | 66.67% |
| 11 | 10 | 0 | 10 | 66.67% |
| 12 | 10 | 0 | 10 | 66.67% |
| 13 | 10 | 2 | 8 | 53.33% |

Example 9

Treatment Efficacy Study in Animal Model

Kuiking mice were used in this study. The average weight of the mice used in this study is about 23 grams. About $10^3$ liver cancer cells were implanted into the left army pit of mice. At about 10 days, the small tumor grew under the mice skin. At about 15 days, the tumor grew to about 1 cm size. The mice were divided into three groups: control group, therapy group and immunotherapy group. In the control group, 0.1 ml of Ara-C in normal saline was injected to the tumor via intro-tumor injection. The results of the studies conducted in the control group were summarized in the following Table 14.

TABLE 14

| | | | | Control group | | | |
|---|---|---|---|---|---|---|---|
| No. | | Date | 1 d | 2 d | 3 d | 4 d | |
| 1 | Weight | 20 | 23.5 | 21 | 20 | 24 | |
| | TV Scm | 0.7*0.7*0.5 = 0.245 | 1.1*0.7*0.6 = 0.462 | 1.3*0.9*0.6 = 0.702 | 1*1*0.6 = 0.6 | 1*1*0.7 = 0.7 | |
| 2 | Weight | 26 | 27 | 25 | 23.5 | 28.5 | |
| | TV Scm | 0.8*0.6*0.4 = 0.192 | 1.3*0.7*0.5 = 0.455 | 1.2*1.1*0.8 = 1.1 | 1.1*1.2*0.7 = 0.924 | 1.3*1.4*1.1 = 2 | |
| 3 | Weight | 23.5 | 25 | 24 | 22 | 26.5 | |
| | TV Scm | 1*0.5*0.3 = 0.15 | 1.1*0.8*0.6 = 0.528 | 1.2*0.9*0.5 = 0.54 | 1.3*0.8*0.4 0.416 | 1.5*1*0.6 = 0.99 | |
| 4 | Weight | 24 | 25 | 24 | 22 | 24 | |
| | TV Scm | 1.3*0.9*0.6 = 0.7 | 1.4*1.1*1 = 1.54 | 1.4*1.2*0.8 = 1.34 | 1.5*1.2*1 = 1.8 | 1.6*1.4*1 = 2.24 | |
| 5 | Weight | 22.5 | 25 | 19 | 22 | 28.2 | |
| | TV Scm | 1*0.7*0.5 = 0.35 | 1*0.9*0.6 = 0.54 | 1*0.8*0.6 = 0.48 | 1.2*0.9*0.6 = 0.648 | 1.2*0.8*0.5 = 1 | |
| 6 | Weight | 18 | 20 | 19 | 17.5 | 22.8 | |
| | TV Scm | 0.9*0.7*0.5 = 0.32 | 1.1*1*0.7 = 0.77 | 1.3*0.6*0.5 = 0.39 | 1.2*1.1*0.8 = 1.1 | 1.6*1.3*1.4 = 2.9 | |

TABLE 14-continued

| | | Control group | | | | |
|---|---|---|---|---|---|---|
| 7 | Weight | 18.5 | 21 | 16.5 | 17 | 15.8 |
| | TV Scm | 0.8*0.6*0.5 = 0.24 | 1.2*1*0.8 0.96 | 1.3*1*0.8 = 1.04 | 1.2*1*0.6 = 0.72 | 1.4*0.8*0.6 = 0.67 |
| 8 | Weight | 14 | 17 | 17 | 15 | 16.5 |
| | TV Scm | 1*0.9*0.6 = 0.54 | 1.5*1*0.9 1.35 | 1.3*0.8*0.7 = 0.73 | 1.5*1.2*1 = 1.8 | 1.5*1.2*1.1 = 1.98 |
| 9 | Weight | 23 | 25.5 | 23.8 | 22 | 26 |
| | TV Scm | 1*0.8*0.5 = 0.4 | 1.3*0.9*0.8 = 0.94 | 1.2*1.1*0.8 = 1.06 | 1.4*1.1*0.7 = 1.08 | 1.2*1.1*0.8 = 1.06 |
| 10 | Weight | 14.5 | 18 | 17.5 | 16.5 | 20 |
| | TV Scm | 0.7*0.7*0.6 = 0.294 | 1*0.7*0.7 = 0.49 | 1.2*1*0.8 = 0.96 | 1.4*1.2*0.8 = 1.34 | 1.3*1.1*0.8 = 1.14 |
| Everage | TV1 | 0.343 | 0.8 | 1.33 | 1.47 | 1.47 |

| No. | □□ | 5 d | 6 d | 7 d | 8 d | 9 d |
|---|---|---|---|---|---|---|
| 1 | Weight | 24.5 | 23.5 | 24 | 24.5 | 24.5 |
| | TV Scm | 1.4*1*1 = 1.4 | 1.3*1.1*0.8 = 1.14 | 1.5*0.8*0.7 = 0.84 | 1.3*0.9*0.7 = 0.819 | 1.5*1.2*0.9 = 1.62 |
| 2 | Weight | 30 | 31 | 32.5 | 33 | 33.5 |
| | TV Scm | 1.5*1.3*1 = 1.95 | 1.6*1.3*1.1 = 2.28 | 1.8*1.6*1.5 = 4.32 | 1.4*1.5*1.3 = 2.73 | 1.8*1.8*1.8 = 5.8 |
| 3 | Weight | 28.5 | 29.5 | 29 | 24 | 23.5 |
| | TV Scm | 1.5*1.1*0.7 = 1.16 | 1.2*1*0.5 = 0.6 | 1.4*0.9*0.6 = 0.76 | 1.8*1.2*1.2 = 2.59 | 1.9*1.5*1.4 = 3.99 |
| 4 | Weight | 24 | 24.5 | 24.5 | 28.5 | 28.5 |
| | TV Scm | 1.7*1.3*0.9 = 1.98 | 1.8*1.2*1 = 2.16 | 1.9*1.4*1.2 = 3.19 | 1.2*0.7*0.6 = 0.5 | 1.6*1.1*0.7 = 1.2 |
| 5 | Weight | 28 | 28 | 28.5 | 24.5 | 24.5 |
| | TV Scm | 1.2*1.2*0.7 = 1 | 1.3*1.5*0.6 = 1.17 | 1.5*1.3*0.9 = 1.76 | 1.5*1.5*1.2 = 2.7 | 2.1*1.5*1.4 = 4.4 |
| 6 | Weight | 24 | 24 | 24 | 24.5 | 28.5 |
| | TV Scm | 1.5*1.3*0.9 = 1.75 | 1.6*1.4*1 = 2.24 | 1.9*1.5*1 = 2.85 | 1.5*1.6*1.4 = 3.36 | 1.3*1.4*1.1 = 2 |
| 7 | Weight | □□ | | | | |
| | TV Scm | | | | | |
| 8 | Weight | 19 | 19 | 19.5 | 20 | 21 |
| | TV Scm | 1.7*1.4*1 = 2.38 | 1.9*1.6*1.2 = 3.6 | 1.8*1.5*1.5 = 4 | 1.5*1.3*1.2 = 2.34 | 1.7*1.4*1.1 = 2.62 |
| 9 | Weight | 26.5 | 28 | 28 | 28.5 | 29 |
| | TV Scm | 1.4*1.4*1 = 1.96 | 1.5*1.4*1.1 = 2.31 | 1.5*1.4*1.3 = 2.73 | 1.5*1.4*1.2 = 2.52 | 1.4*1.6*1.4 = 3.14 |
| 10 | Weight | 21.5 | 22 | 21 | 21 | 23 |
| | TV Scm | 1.6*1*0.8 = 1.28 | 1.4*1.2*0.8 = 1.34 | 1.5*1.6*1.2 = 2.88 | 1.5*1.2*1.1 = 1.98 | 1.8*1.4*1.3 = 3.28 |
| Everage | TV1 | 1.65 | 1.87 | 2.59 | 2.73 | 3.12 |

Scm = Sq cm,
TV = tumor volume

In the therapy group, 0.1 ml of the combination of ethanol, $H_2O_2$, anticancer drug AraC and hemotoxilin in normal saline was injected to the tumor via intro-tumor injection. The results of the studies conducted in the therapy group was summarized in the following Table 15.

TABLE 15

| | | Therapy group | | | | |
|---|---|---|---|---|---|---|
| No. | Kind | Date | 1 d | 2 d | 3 d | 4 d |
| 1 | Weight | 17 | 18 | 20 | 20.5 | 22 |
| | TV Scm | 0.7*0.6*0.6 | 0.8*0.8*0.6 | 0.9*0.7*0.6 | 0.9*1.1*0.6 | 1.1*1.1*0.8 |
| | TV | 0.252 | 0.384 | 0.378 | 0.594 | 0.968 |
| 2 | Weight | 19 | 21 | 22 | 23.5 | 24 |
| | TV Scm | 0.7*0.7*0.5 | 1.2*1.0*0.8 | 1.0*0.8*0.6 | 1.0*0.9*0.6 | 1.0*0.8*0.7 |
| | TV | 0.245 | 0.96 | 0.48 | 0.54 | 0.56 |

TABLE 15-continued

| | | Therapy group | | | | |
|---|---|---|---|---|---|---|
| 3 | Weight | 22 | 25 | 25.5 | 26.5 | 27 |
| | TV | 1.2*0.7*0.6 | 1.2*0.9*0.8 | 1.1*0.8*0.6 | 1.3*1.4*1.0 | 1.6*1.6*1.3 |
| | Scm | | | | | |
| | TV | 0.504 | 0.864 | 0.528 | 1.82 | 3.328 |
| 4 | Weight | 21 | 23 | 23 | 24 | 24 |
| | TV | 0.9*0.8*0.6 | 1.1*0.9*0.9 | 0.9*1*0.6 | 1.1*1.1*0.6 | 0.8*0.7*0.6 |
| | Scm | | | | | |
| | TV4 | 0.432 | 0.891 | 0.54 | 0.726 | 0.336 |
| 5 | Weight | 24 | 28.5 | 28 | 29 | 30 |
| | TV | 1.1*0.8*0.6 | 1.2*0.8*0.7 | 0.9*0.8*0.7 | 1.2*1.1*1 | 1.1*1*0.8 |
| | Scm | | | | | |
| | TV | 0.528 | 0.672 | 0.504 | 1.32 | 0.88 |
| 6 | Weight | 23 | 26 | 25 | 27 | 27 |
| | TV | 0.5*0.6*0.5 | 1.1*0.9*0.8 | 0.8*0.7*0.6 | 1*0.7*0.5 | 0.9*0.7*0.5 |
| | Scm | | | | | |
| | TV | 0.15 | 0.792 | 0.336 | 0.35 | 0.315 |
| 7 | Weight | 23 | 27 | 27 | 28.5 | 28.5 |
| | TV | 0.7*0.7*0.6 | 0.9*0.6*0.5 | 0.8*0.4*0.5 | 0.7*0.6*0.5 | 0.9*0.7*0.6 |
| | Scm | | | | | |
| | TV | 0.294 | 0.27 | 0.16 | 0.21 | 0.378 |
| 8 | Weight | 24 | 29.5 | 31 | 30.5 | 32 |
| | TV | 0.6*0.5*0.4 | 0.6*0.6*0.5 | 0.8*0.7*0.5 | 0.8*0.7*0.4 | 0.9*0.7*0.5 |
| | Scm | | | | | |
| | TV | 0.12 | 0.18 | 0.28 | 0.224 | 0.315 |
| 9 | Weight | 20 | 22 | 22.5 | 23.5 | 24 |
| | TV | 0.8*0.7*0.5 | 0.9*0.9*0.7 | 1*0.9*0.5 | 1*0.8*0.6 | 1.1*1.1*0.8 |
| | Scm | | | | | |
| | TV9 | 0.15 | 0.792 | 0.336 | 0.35 | 0.315 |
| EV | TV Scm | 0.645 | 0.39 | 0.68 | 1.15 | 0.788 |

| No. | Kind | 5 d | 6 d | 7 d | 8 d | 9 d |
|---|---|---|---|---|---|---|
| 1 | Weight | 22.5 | 23 | 23 | 23.5 | 23.5 |
| | TV | 1.5*1.2*0.9 | 1.4*1.2*0.9 | 1.3*1.4*1.2 | 1.3*1.3*1.1 | 1.6*1.3*1.1 |
| | Scm | | | | | |
| | TV | 1.62 | 1.512 | 2.184 | 1.859 | 2.288 |
| 2 | Weight | 24 | 24.5 | 25 | 26 | 25.5 |
| | TV | 0.8*0.8*0.6 | 1.0*0.9*0.6 | 1.0*1.1*0.8 | 1.3*1.0*0.9 | 1.2*1.3*1.1 |
| | Scm | | | | | |
| | TV | 0.384 | 0.54 | 0.88 | 1.17 | 1.716 |
| 3 | Weight | 28 | 29 | 29 | 29.5 | 29.5 |
| | TV | 1.5*1.3*1.0 | 1.7*1.5*1.1 | 1.9*1.8*1.7 | 2.5*1.8*1.6 | 2.4*1.7*1.9 |
| | Scm | | | | | |
| | TV | 1.95 | 2.805 | 5.814 | 7.2 | 7.752 |
| 4 | Weight | 25.5 | 25.5 | 26 | 26.5 | 26 |
| | TV | 1.2*1.2*0.6 | 1*0.9*0.6 | 1.1*0.9*0.6 | 1.4*1.3*0.9 | 1.2*1.4*1.1 |
| | Scm | | | | | |
| | TV4 | 0.864 | 0.54 | 0.594 | 1.638 | 1.848 |
| 5 | Weight | 31 | 32 | 31 | 32 | 31.5 |
| | TV | 1.3*0.9*0.6 | 1.4*1.2*0.9 | 1.4*1*0.7 | 1.5*1.1*0.8 | 1.5*0.9*0.7 |
| | Scm | | | | | |
| | TV | 0.702 | 1.512 | 0.98 | 1.32 | 0.945 |
| 6 | Weight | 27.5 | 27.5 | 27.5 | 29.5 | 27.5 |
| | TV | 1*0.7*0.6 | 1*0.9*0.6 | 1.1*1*0.9 | 1.6*1.1*1.0 | 1.5*1.2*1 |
| | Scm | | | | | |
| | TV | 0.42 | 0.54 | 0.99 | 1.76 | 1.8 |
| 7 | Weight | 28.5 | 29 | 29.5 | 30 | 30 |
| | TV | 1.2*0.7*0.5 | 1.2*0.9*0.6 | 1.23*1*0.7 | 1.2*1.3*1 | 1.2*1.1*0.8 |
| | Scm | | | | | |
| | TV | 0.42 | 0.648 | 0.861 | 1.56 | 1.056 |
| 8 | Weight | 31 | 32.5 | 34 | 34 | 34 |
| | TV | 0.8*0.8*0.5 | 1*0.9*0.6 | 0.9*1*0.5 | 0.9*1*0.7 | 1*1*0.8 |
| | Scm | | | | | |
| | TV | 0.32 | 0.54 | 0.45 | 0.63 | 0.8 |
| 9 | Weight | 24 | 25 | 24 | 25 | 25 |
| | TV | 1.2*1*0.6 | 1.2*1.2*0.8 | 1.4*1.1*0.8 | 1.4*1.3*0.9 | 1.5*1.2*1.1 |
| | Scm | | | | | |
| | TV9 | 0.42 | 0.54 | 0.99 | 1.76 | 1.8 |
| EV | TV Scm | 1.019 | 1.52 | 2.099 | 2.222 | 0.393 |

In the immunotherapy group, 0.1 ml of the combination of ethanol, $H_2O_2$, anticancer drug AraC, hemotoxilin and TNP in normal saline was injected to the tumor via intro-tumor injection. The results of the studies conducted in the immunotherapy was summarized in the following Table 16.

TABLE 16

| | | Immunotherapy group | | | | |
|---|---|---|---|---|---|---|
| No. | Kind | Date | 1 d | 2 d | 3 d | 4 d |
| 1 | Weight | 24 | 23 | 23 | 25 | 24 |
| | TV | 0.6*0.4*0.4 | 0.7*0.6*0.5 | 0.7*0.6*0.5 | 1*0.8*0.6 | 0.9*0.8*0.6 |
| | TV1 | 0.096 | 0.21 | 0.21 | 0.48 | 0.432 |
| | Scm | | | | | |
| 2 | Weight | 29 | 28.5 | 30 | 32 | 32 |
| | TV | 1*0.6*0.5 | 1.3*1.3*1.1 | 1.3*1.3*1 | 0.7*0.6*1.7 | 1.6*1.4*1.3 |
| | Scm | 0.3 | 1.859 | 1.69 | 0.714 | 2.912 |
| 3 | Weight | 25 | 27 | 27.5 | 28 | 28.5 |
| | TV | 0.7*0.6*0.5 | 1.2*1.2*1 | 1.1*0.7*0.7 | 1.1*1*0.8 | 0.8*1.2*0.9 |
| | Scm | 0.21 | 1.44 | 0.539 | 0.88 | 0.864 |
| 4 | Weight | 26 | 28 | 28.5 | 30 | 30 |
| | TV | 0.9*0.7*0.5 | 0.7*0.6*0.5 | 0.7*0.7*0.6 | 0.8*0.7*0.6 | 0.7*0.7*0.6 |
| | Scm | 0.315 | 0.21 | 0.294 | 0.336 | 0.294 |
| 5 | Weight | 24 | 27 | 27 | 28 | 28 |
| | TV | 0.7*0.6*0.5 | 0.6*0.5*0.4 | 0.7*0.8*0.6 | 0.8*0.8*0.5 | 0.8*0.8*0.5 |
| | Scm | 0.21 | 0.12 | 0.336 | 0.32 | 0.32 |
| 6 | Weight | 26 | 28 | 27.5 | 28.5 | 29 |
| | TV | 0.5*0.4*0.3 | 1*1*0.8 | 0.6*0.6*0.5 | 0.8*0.7*0.5 | 0.9*0.9*0.7 |
| | Scm | 0.06 | 0.8 | 0.18 | 0.28 | 0.567 |
| 7 | Weight | 24 | 24 | 24 | 24.5 | 24 |
| | TV | 0.7*0.7*0.5 | 0.8*0.6*0.5 | 0.7*0.6*0.6 | 0.8*0.6*0.4 | 0.9*0.7*0.6 |
| | Scm | 0.245 | 0.24 | 0.252 | 0.192 | 0.378 |
| 8 | Weight | 18.5 | 18 | 17.5 | 17.8 | 17.5 |
| | TV | 0.8*0.7*0.6 | 0.8*0.6*0.6 | 1*0.7*0.6 | 1.2*0.9*0.6 | 1.3*1.1*1 |
| | Scm | 0.336 | 0.288 | 0.42 | 0.648 | 1.43 |
| 9 | Weight | 16 | 16 | 17 | 17.5 | 18.5 |
| | TV | 0.8*0.6*0.5 | 0.7*0.7*0.5 | 0.7*0.7*0.6 | 1*0.9*0.6 | 0.8*0.8*0.6 |
| | Scm | 0.24 | 0.245 | 0.294 | 0.54 | 0.384 |
| EV | TV | 0.223 | 0.601 | 0.468 | 0.487 | 0.842 |
| No. | Kind | 5 d | 6 d | 7 d | 8 d | 9 d |
| 1 | Weight | 25 | 24.5 | 25 | 25 | 24.5 |
| | TV | 0.8*0.6*0.5 | 1.1*1*0.8 | 1.2*0.9*0.8 | 1.4*1.1*0.7 | 1.3*1.1*0.7 |
| | TV1 | 0.24 | 0.88 | 0.864 | 1.078 | 1.001 |
| | Scm | | | | | |
| 2 | Weight | 32.8 | 32 | 31 | 31 | □□ |
| | TV | 1.5*1.5*1.1 | 1.9*1.6*1.8 | 2.3*1.8*2 | 2*1.7*1.6 | |
| | Scm | 2.475 | 5.472 | 8.28 | 5.44 | |
| 3 | Weight | 29.5 | 29 | 28 | 28.5 | 29 |
| | TV | 1*1*0.8 | 1.3*1*0.9 | 0.8*1.1*0.7 | 1*1.2*1 | 0.9*1*0.9 |
| | Scm | 0.8 | 1.17 | 0.616 | 1.2 | 0.81 |
| 4 | Weight | 31 | 30.5 | 31 | 31.5 | 31.5 |
| | TV | 0.7*0.6*0.5 | 0.9*0.7*0.6 | 0.9*0.8*0.6 | 1*1*0.8 | 0.9*1*0.7 |
| | Scm | 0.21 | 0.378 | 0.432 | 0.8 | 0.63 |
| 5 | Weight | 28 | 28 | 27.5 | 28 | 27.5 |
| | TV | 0.9*0.8*0.7 | 0.9*1.2*0.7 | 1*1.1*0.7 | 1.1*1.1*1 | 1.2*1.4*1 |
| | Scm | 0.504 | 0.756 | 0.77 | 1.21 | 1.68 |
| 6 | Weight | 29 | 29.5 | 29.5 | 30.5 | 30 |
| | TV | 0.9*0.8*0.6 | 1.2*1*0.9 | 1.3*1*1 | 1.3*1.1*0.9 | 1.4*1.2*1.1 |
| | Scm | 0.432 | 1.08 | 1.3 | 1.287 | 1.848 |
| 7 | Weight | 24.5 | 24.5 | 24 | 25 | 25 |
| | TV | 1*0.7*0.4 | 1.1*1*0.6 | 1.1*0.8*0.5 | 1.4*1.1*0.8 | 1.1*0.9*0.8 |
| | Scm | 0.28 | 0.66 | 0.44 | 1.232 | 0.792 |
| 8 | Weight | 19 | 17.5 | 18.5 | 19.5 | 19.5 |
| | TV | 0.9*0.6*0.5 | 1.5*1.2*1 | 1.5*1.2*1.2 | 1.7*1.4*1.2 | 1.8*1.4*1.3 |
| | Scm | 0.27 | 1.8 | 2.16 | 2.856 | 3.276 |
| 9 | Weight | 17.8 | 18.5 | 19 | 19.5 | 19.5 |
| | TV | 1.1*0.9*0.6 | 1*0.7*0.5 | 1.1*1.1*0.7 | 1.4*1*0.8 | 1.1*1*0.8 |
| | Scm | 0.594 | 0.35 | 0.847 | 1.232 | 0.88 |
| EV | TV | 0.645 | 1.394 | 1.745 | 1.815 | 1.364 |

EV = Average,
TV = Tumor Volume

Figure 3:
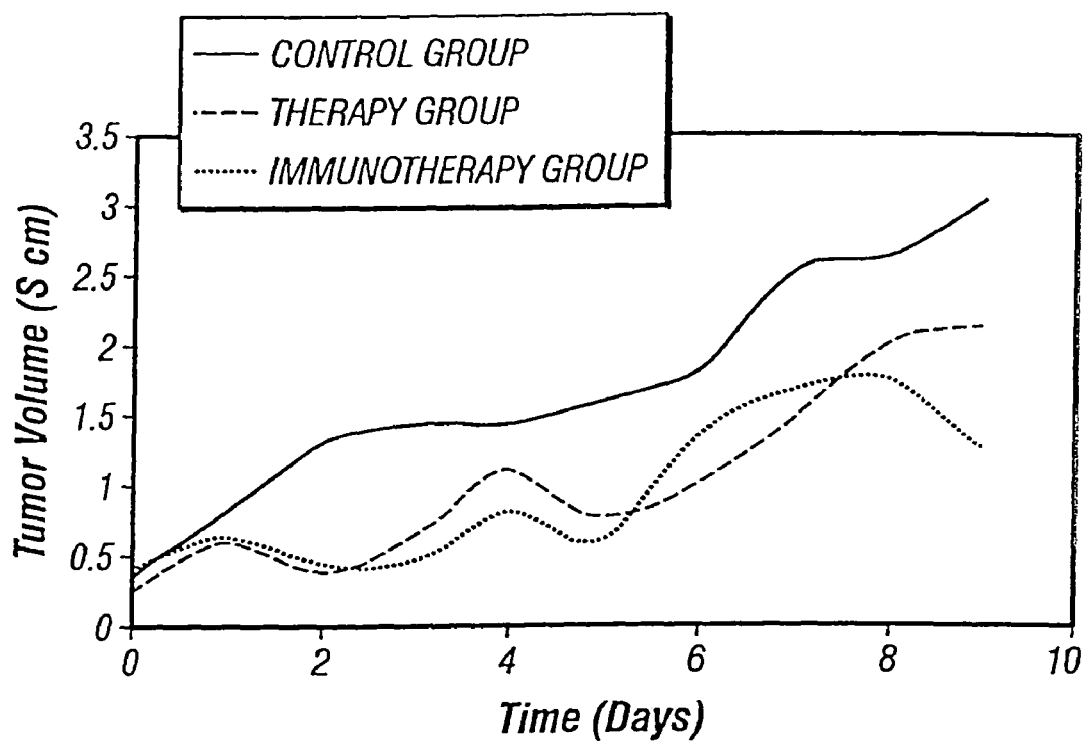
FIG. 3 shows the result of a treatment study in mice.

The results of the control group, therapy group and immunotherapy group are also illustrated in the FIG. 3. As illustrated in FIG. 3, the tumor size in both the immunotherapy and the therapy was substantially smaller than that in the control group within the 10 day period.

Example 10

Radioisotope Retaining Study in Animal Model

Figure 4:
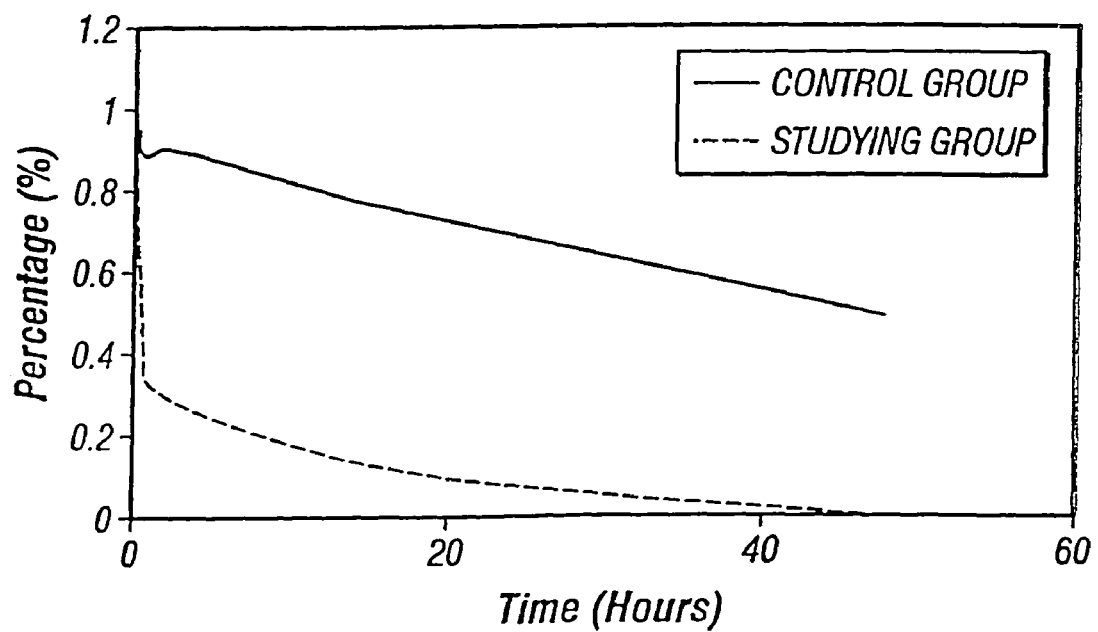
FIG. 4 shows the result of a radioisotope retaining study in mice.

In the control group, 0.1 ml of 24 μci $^{99}$mTc free isotope in normal saline was intro-tumor injected to each tumor of the mice. In the studying group, 0.1 ml of 24 μci $^{99}$mTc in the formulation described in the Examples 1-2, e.g., the combination of ethanol, $H_2O_2$, Ara-C and hemotoxilin, was intro-tumor injected to each tumor of the mice. After the intro-tumor injection, the mice were placed into the frame under Gama Camera to start imaging studying. Pictures at 10, 15, 30, 60, 120 minutes and 19 and 48 hours were taken. The Interest of Area (IOA) on the tumor and whole body for calculating Gama Count of $^{99}$mTc were drawn by computer. Retaining percentage is calculated as the ratio of tumor IOA/whole body IOA* %. The results are illustrated in FIG. 4. In the control group, $^{99}$mTc starts to diffuse out of tumor at 10 min. At 30 min., more than 50% of isotope comes out of tumor in the control group. In studying group, 90% of the isotope remains inside the tumor center at 10 min. At 2 hours, only 30% of the isotope is left inside the tumor in the control group while about 90% of the isotope is still kept inside the tumor in the studying group. At 19 hours, the $^{99}$mTc isotope disappears from tumor in the control group. In contrast, at 48 hours, about 50% of the $^{99}$mTc isotope is still kept inside the tumor (See FIG. 4).

Since modifications will be apparent to those of skill in this art, it is intended that this invention be limited only by the scope of the appended claims.

The invention claimed is:

1. A combination, comprising:
    a) an oxidizing agent or a reducing agent;
    b) a protein denaturing agent; and
    c) a hapten;
    wherein said combination is formulated for injectable delivery into a neoplasm of a mammal.

2. A kit, comprising the combination of claim 1.

3. An article of manufacture, comprising:
    a) packaging material;
    b) a combination comprising:
        i) an oxidizing agent or a reducing agent;
        ii) a protein denaturing agent; and
        iii) a hapten selected from the group consisting of trinitrophenol (TNP), dinitrophenol (DNP), N-iodoacetyl-N'-(5-sulfonic 1-naphthyl) ethylene diamine (AED), and dinitrofluorobenzene(DNFB); and
    c) a label indicating that the article is for treating neoplasms.

4. A method for treating neoplasm in a mammal, comprising in situ administering to neoplasm of a mammal an effective amount of (1) a hapten, and (2) coagulation agent(s) or treatment(s) that causes coagulation of the neoplasm, whereby an autologous immune response is generated against the neoplasm and the neoplasm is treated;
    wherein the hapten and coagulation agent(s) are administered to the neoplasm via injection or in combination with a surgical procedure; and
    wherein the hapten is selected from the group consisting of trinitrophenol (TNP), dinitrophenol (DNP), N-iodoacetyl-N'-(5-sulfonic 1-naphthyl) ethylene diamine (AED), and dinitrofluorobenzene(DNFB).

5. The method of claim 4, wherein the coagulation agent(s) is selected from the group consisting of:
    a) an oxidizing agent or a reducing agent; and
    b) an oxidizing agent or a reducing agent, and a protein denaturing agent.

6. The method of claim 5, wherein the oxidizing or reducing agent, the protein denaturing agent and the hapten are formulated in a single pharmaceutical composition or each is formulated in a separate pharmaceutical composition.

7. The method of claim 5, wherein the oxidizing agent is selected from the group consisting of hydrogen peroxide ($H_2O_2$), ozone, $NaIO_4$, potassium peroxymonosulfate (oxone), D,L-S-methyllipoic acid methyl ester, tertiary butyl hydroperoxide, carbamide peroxide, menadione, diamide, iodogen, N-bromosuccinimide, omeprazole and N-ethylmaleimide.

8. The method of claim 5, wherein the protein denaturing agent is selected from the group consisting of an alcohol, guanidine hydrochloride, guanidinium thiocyanate, sodium citrate, 2-mercaptoethanol, sarcosyl, phenol, chloroform and urea.

9. The method of claim 5, wherein the method further comprises in situ administering to neoplasm of a mammal an effective amount of an anti-neoplasm agent.

10. The method of claim 9, wherein the anti-neoplasm agent is selected from the group consisting of an alkylating agent, an antimetabolite, a natural product, a platinum coordination complex, an anthracenedione, a substituted urea, a methylhydrazine derivative, Mitotane (o,p'-DDD), a hormone and an antagonist.

11. The method of claim 5, wherein the oxidizing agent is $H_2O_2$, the protein denaturing agent is ethanol and the hapten is DNP.

12. The method of claim 5, wherein the oxidizing agent or reducing agent is from about 0.01% (w/w) to about 35% (w/w), the protein denaturing agent is from about 1% (w/w) to about 99% (w/w) and the hapten is from about 1 mg/ml to about 80 mg/ml.

13. The combination of claim 1, wherein the hapten is selected from the group consisting of trinitrophenol (TNP), dinitrophenol (DNP), N-iodoacetyl-N'-(5-sulfonic 1-naphthyl) ethylene diamine (AED), and dinitrofluorobenzene(DNFB).

14. The combination of claim 1, wherein the oxidizing or reducing agent, the protein denaturing agent and the hapten are formulated in a single pharmaceutical composition or each is formulated in a separate pharmaceutical composition.

15. The combination of claim 1, wherein the oxidizing agent is selected from the group consisting of hydrogen peroxide ($H_2O_2$), ozone, $NaIO_4$, potassium peroxymonosulfate (oxone), D,L-S-methyllipoic acid methyl ester, tertiary butyl hydroperoxide, carbamide peroxide, menadione, diamide, iodogen, N-bromosuccinimide, omeprazole and N-ethylmaleimide.

16. The combination of claim 1, wherein the protein denaturing agent is selected from the group consisting of an alcohol, guanidine hydrochloride, guanidinium thiocyanate, sodium citrate, 2-mercaptoethanol, sarcosyl, phenol, chloroform and urea.

17. The combination of claim 1, wherein the combination further comprises an anti-neoplasm agent.

18. The combination of claim 17, wherein the anti-neoplasm agent is selected from the group consisting of an alkylating agent, an antimetabolite, a natural product, a platinum coordination complex, an anthracenedione, a substituted urea, a methylhydrazine derivative, Mitotane (o,p'-DDD), a hormone and an antagonist.

19. The combination of claim 1, wherein the oxidizing agent is $H_2O_2$, the protein denaturing agent is ethanol and the hapten is DNP.

20. The combination of claim 1, wherein the oxidizing agent or reducing agent is from about 0.01% (w/w) to about 35% (w/w), the protein denaturing agent is from about 1% (w/w) to about 99% (w/w) and the hapten is from about 1 mg/ml to about 80 mg/ml.

21. The method of claim 4, wherein the coagulation comprises carbamide peroxide and/or a chitosan.

22. The method of claim 21, wherein the chitosan is a chitosan oligosaccharide or a water soluble chitosan.

23. The method of claim 22, wherein the hapten is selected from the group consisting of trinitrophenol (TNP), dinitrophenol (DNP), N-iodoacetyl-N'-(5-sulfonic 1-naphtyl) ethylene diamine (AED), and dinitrofluorobenzene(DNFB).

24. The method of claim 5, wherein the oxidizing agent is carbamide peroxide, the protein denaturing agent is ethanol and the hapten is DNP.

25. The combination of claim 1, wherein the oxidizing agent is carbamide peroxide, the protein denaturing agent is ethanol and the hapten is DNP.

26. The method of claim 4, wherein the mammal is a human.

\* \* \* \* \*